US006761688B1

(12) United States Patent
Mohr, III et al.

(10) Patent No.: US 6,761,688 B1
(45) **Date of Patent: *Jul. 13, 2004**

(54) MULTI-LAYERED TRANSDUCER ARRAY AND METHOD HAVING IDENTICAL LAYERS

(75) Inventors: John P. Mohr, III, San Jose, CA (US); Worth B. Walters, Cupertino, CA (US); Sevig Ayter, Cupertino, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 253 days.

This patent is subject to a terminal disclaimer.

(21) Appl. No.: 09/796,986

(22) Filed: Feb. 28, 2001

(51) Int. Cl.[7] .................................................. A61B 8/00

(52) U.S. Cl. ........................ 600/437; 600/459; 310/334

(58) Field of Search ................................ 600/437, 438, 600/440–447, 449–459, 461, 462–471; 310/333, 334, 365; 29/25.35; 73/618–641; 367/153, 157, 173, 174, 180; 381/113, 150, 173, 190

(56) References Cited

U.S. PATENT DOCUMENTS

| | | | |
|---|---|---|---|
| 3,281,613 | A | 10/1966 | Hatschek |
| 3,390,287 | A | 6/1968 | Sonderegger |
| 4,217,684 | A | 8/1980 | Brisken et al. |
| 4,845,399 | A | 7/1989 | Yasuda et al. |
| 5,115,809 | A | 5/1992 | Saitoh et al. |
| 5,163,436 | A | 11/1992 | Saitoh et al. |
| 5,349,262 | A | 9/1994 | Grenon et al. |
| 5,381,385 | A | 1/1995 | Greenstein |
| 5,406,164 | A | 4/1995 | Okawa et al. |
| 5,410,205 | A | 4/1995 | Gururaja |
| 5,410,208 | A | 4/1995 | Walters et al. |
| 5,415,175 | A | 5/1995 | Hanafy et al. |
| 5,438,998 | A | 8/1995 | Hanafy |

(List continued on next page.)

OTHER PUBLICATIONS

"A Dual Frequency Ultrasonic Probe," S. Saitoh et al., Research and Development Center, Toshiba Corporation, Kawasaki, Kanagawa 210, pp. 172–174 (1991).

"Special Issue Correspondence," M. Greenstein et al., IEEE Translations on Ultrasonics Ferroelectrics and Frequency Control, vol. 43, No. 4, pp. 620–622 (1996).

"Multi–Layer PZT Transducer Arrays for Improved Sensitivity," R. Goldberg, et al., Ultrasonics Symposium, pp. 551–554, (1992).

"A Low–Impedance Ultrasonic Probe Using a Multilayer Piezoelectric Ceramic." S. Saitoh et al., Japanese Journal of Applied Physics, vol. 28 Supplement 23–I, pp. 56–56 (1989)).

"Multilayer Thin Film Piezoelectric Transducers," J. De Klerk, IEEE Transactions on Sonics and Ultrasonics, vol. SU–13, No. 3, pp. 99–103, (1966).

(List continued on next page.)

*Primary Examiner*—Ali Imam

(57) ABSTRACT

Multiple layer elements for a transducer array are provided. Each element comprises two or more layers of transducer material. Various of the elements include one or more of: (1) multiple-layer, multiple-dimensional arrays where the layers are polymericly bonded and electrically connected through asperity contact, (2) multiple layer array of elements where air or gas separates at least two elements, (3) an even number of layers where each layer is electrically connected through asperity contact, (4) multiple-layers where each layer comprises transducer material and electrodes in a substantially same configuration, and (5) electrically isolating electrodes on layers by kerfing or cutting after bonding the layers together.

40 Claims, 12 Drawing Sheets

U.S. PATENT DOCUMENTS

| | | | |
|---|---|---|---|
| 5,459,371 | A | 10/1995 | Okawa et al. |
| 5,490,512 | A | 2/1996 | Kwon et al. |
| 5,534,092 | A | 7/1996 | Ogawa et al. |
| 5,548,564 | A | 8/1996 | Smith |
| 5,549,778 | A | 8/1996 | Yokoyama et al. |
| 5,575,290 | A | 11/1996 | Teo et al. |
| 5,597,494 | A | 1/1997 | Kohno et al. |
| 5,598,051 | A | 1/1997 | Frey |
| 5,603,147 | A | 2/1997 | Bischoff et al. |
| 5,671,746 | A | 9/1997 | Dreschel et al. |
| 5,678,554 | A | 10/1997 | Hossack et al. |
| 5,704,105 | A | 1/1998 | Venkataramani et al. |
| 5,706,820 | A | 1/1998 | Hossack et al. |
| 5,724,976 | A | 3/1998 | Mine et al. |
| 5,744,898 | A | 4/1998 | Smith et al. |
| 5,840,032 | A | 11/1998 | Hatfield et al. |
| 5,844,349 | A | 12/1998 | Oakley et al. |
| 5,846,201 | A | 12/1998 | Adams |
| 5,882,309 | A | 3/1999 | Chiao et al. |
| 5,894,646 | A | 4/1999 | Hanafy et al. |
| 5,897,501 | A | 4/1999 | Wildes et al. |
| 5,911,221 | A | 6/1999 | Teo |
| 5,957,851 | A | 9/1999 | Hossack |
| 6,121,718 | A | 9/2000 | Mohr, III |
| 6,429,574 | B1 * | 8/2002 | Mohr et al. ................. 310/334 |
| 6,437,487 | B1 * | 8/2002 | Mohr et al. ................. 310/365 |

OTHER PUBLICATIONS

"Transmission Parameters of Thickness–Driven Piezoelectric Transducers Arranged in Multilayer Configurations," E. Sittig, IEEE Transactions on Sonics and Ultrasonics, vol. SU–14, No. 4, pp. 167–174, (1967).

"Multilayer Piezoelectric Ceramics for Two–Dimensional Array Transducers," R. Goldberg, IEEE Transactions, Ferroelectrics, and Frequency Control, vol. 41, No. 5, pp. 761–771, (1994).

"Optimization of Signal–to Noise Ration for Multilayer PZT Transducers." R. Goldberg, Ultrasonic Imaging 17, pp. 95–113, (1995).

"A Dual Frequency Ultrasonic Probe for Medical Applications," S. Saitoh, et al., IEEE Translations on Ultrasonics, Ferroelectrics, and Frequency Control, vol. 42, No. 2, pp. 294–300, (1995).

"Multi–Layer Piezoelectric Ceramics for Medical Ultrasound Transducers," R. Goldberg, UMI Dissertation Services, 1994.

* cited by examiner

MULTI-LAYERED TRANSDUCER ARRAY AND METHOD HAVING IDENTICAL LAYERS

BACKGROUND

This invention relates to a multi-layered transducer and method of manufacturing the transducer. For example, a multi-layered, multi-dimensional transducer is used. Multi-dimensional transducer arrays include 1.5-dimensional (1.5D) and 2-dimensional arrays. For example, an array of N×M elements where both N and M are 2 or greater is provided for ultrasonically scanning a patient. 1.5D arrays typically comprise arrays of 64 or 128 azimuthally spaced elements in each of three, five or more elevationally spaced rows.

Multi-dimensional transducer arrays typically have small plate areas or areas for transmitting acoustic energy from the azimuth and elevational plane. Multiple layers account for the small plate areas. The multiple layers are stacked along the range dimension. Multiple layers for each element reduce the electrical impedance when compared to an equivalent element of only one layer. The capacitance of a transducer element increases by the square of the number of layers forming the transducer element. The increased capacitance of the transducer element results in a decrease of the electrical impedance of the transducer element.

In one method of fabricating a multi-layer transducer assembly, sheets of piezoelectric ceramic are formed from raw materials by tape casting. An internal electrode is screen-printed on a sheet of piezoelectric ceramic, and then another sheet of ceramic is laminated on the internal electrode side of the first sheet. External electrodes are printed and fired on the external sides of the first and second sheets. For example, Saithoh, S. et al., "A Dual Frequency Ultrasonic Probe," Jpn. J. Appl. Phys., vol. 31, suppl. 31-1, pp. 172–74 (1992), describes such a method. The signal electrodes are connected to leads using a flex circuit, TABlike jumpers or wire bonding. The ground electrode is connected using a conductive epoxy that contacts the ground electrode and a secondary connector, such as a flex circuit or a metal foil.

Multi-layer transducers are also fabricated with vias to connect similarly oriented layers. Multiple holes are punched mechanically or by laser, drilled or etched into piezoelectric ceramic tape to form the vias on each layer of piezoelectric ceramic. The via holes are filled with a metal paste, and the surface electrodes for each; layer are deposited by screen printing. Multiple layers of green tape are then superimposed to align the vias to form a multi-layer sandwich. The multi-layer sandwich is laminated and sintered to form a single structure. Electrodes are metallized by plating or vacuum deposition on the input pads. For an example of such a process, see U.S. Pat. No. 5,548,564, the disclosure of which is incorporated herein by reference.

BRIEF SUMMARY

The present invention is defined by the following claims, and nothing in this section should be taken as a limitation on those claims. By way of introduction, the preferred embodiment described below includes a multi-layered transducer and method for manufacturing the transducer. Various aspects of the multi-layered transducer elements are discussed below and describe one or more inventions.

Various of the embodiments discussed below include one or more of: (1) multiple-layer, multiple-dimensional arrays where the layers are polymericly bonded and electrically connected through asperity contact, (2) multiple-layer array of elements where air or gas separates at least two elements, (3) an even number of layers where each layer is electrically connected through asperity contact, (4) multiple-layers where each layer comprises transducer material and electrodes in a substantially same configuration, and (5) electrically isolating electrodes on layers by kerfing or cutting after bonding the layers together.

In a first aspect, the multi-layer multiple-dimension transducer is manufactured so that electrodes associated with each of the layers are electrically connected to electrodes of the other layers through asperity contact. By using a particular sequence of cutting and metallizing the sheets for each layer, the appropriate connections through asperity contact of the electrodes are provided. A partial cut along a portion of the azimuthal width but not across the entire azimuthal width of the sheet is made. Depending on the layer, the order of making the partial cuts and metallization is changed. The layers are then stacked and bonded. Since the layers are bonded, filler material is not required, resulting in air between the elevationally spaced elements. Air provides acoustic isolation.

In a second aspect, an even number of layers are electrically connected through asperity contact. Various manufacturing processes including forming discontinuities by cutting and metallizing may be used.

In a third aspect, any of the various multi-layer embodiments comprise layers with discontinuities and transducer material in a same format. By flipping one or more layers relative to another layer and stacking the layers, continuous electrical contact for two or more electrodes is provided for each layer.

In a fourth aspect, any of the various multi-layer embodiments are manufactured by bonding the layers together before electrically isolating some of the electrodes. A kerf is formed in the bonded stack of layers. The kerf extends through one layer and into another. The kerf isolates or forms a majority and minority electrode on one or two layers.

Further aspects and advantages of the invention are discussed below in conjunction with the preferred embodiments.

BRIEF DESCRIPTION OF SEVERAL VIEWS OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

The embodiments discussed below comprise multiple layer elements for a transducer array. Each element comprises two or more layers of transducer material. Various of the embodiments discussed below include one or more of: (1) multiple-layer, multiple-dimensional arrays where the layers are polymericly bonded and electrically connected through asperity contact, (2) multiple layer array of elements where air or gas separates at least two elements, (3) an even number of layers where each layer is electrically connected through asperity contact, (4) multiple-layers where each layer comprises electrodes in a substantially same configuration, and (5) electrically isolating electrodes on layers by kerfing or cutting after bonding the layers together. Each of these embodiments is discussed below in different sections individually or in combination with other embodiments. Other combinations or individual embodiments may be provided.

I. Multi-Dimensional Array with Asperity Contact and Air or Gas Separation

In one embodiment, multiple-dimensional arrays of multiple-layer elements are provided. The multiple layers of transducer material are electrically connected through asperity contact. In at least one dimension, such as the elevation dimension, the various elements are separated by air, acoustically and mechanically isolating the elements. The asperity contact and air separation are provided through a sequence of partial cuts or dicing through each layer and metallization.

Figure 1:
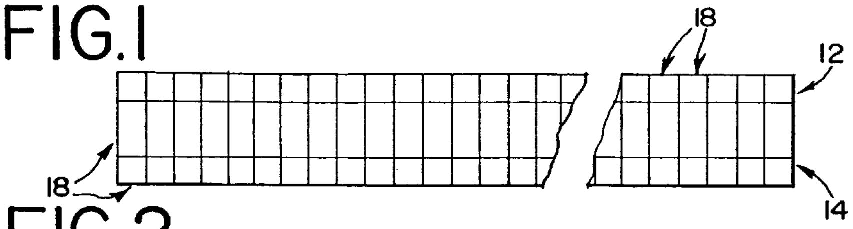
FIG. 1 is a top view of a plane defined by the azimuthal and elevational dimensions of a multi-dimensional transducer array according to one embodiment of the present invention.

FIG. 1 shows a 1.5D transducer array of elements. Three elevationally spaced rows of elements are provided. Sixty-four or 128 azimuthally spaced elements are provided. In alternative embodiments, more or fewer elevationally or azimuthally spaced elements may be used. As shown, the two outer rows of elements 12 and 14 comprise smaller elements (e.g., sub-elements) in the azimuthal elevation plane than the center row 16 of elements. In alternative embodiments, the area of each element may be the same or varied as a function of either azimuth, elevation or range dimensions. In yet another alternative embodiment, a two-dimensional transducer array, such as an array of 64 by 64 elements, or 1.75D array is provided. For a multidimensional array, an array of N×M elements where N and M are greater than 2 is provided. The array may consist of any number of transducer elements 18.

Figure 2:
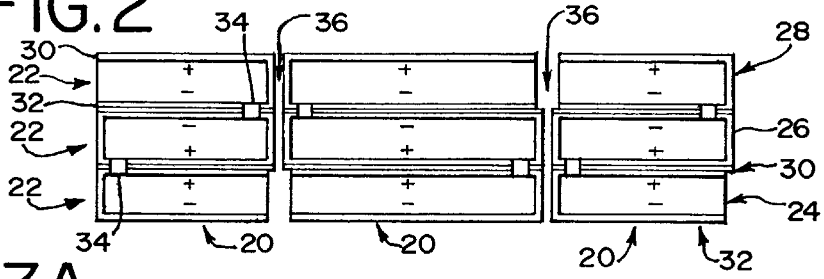
FIG. 2 is a cross-sectional view along the elevation and range dimensions of FIG. 1 of multi-layered transducer elements according to one embodiment of the present invention.

FIG. 2 shows a cross-section of the transducer array of FIG. 1. In particular, three elevationally spaced transducer elements 20 are shown. Each element 20 comprises three layers 22 of transducer material. More or fewer layers may be provided.

The transducer material comprises piezoelectric ceramic, such as a single crystal piezoelectric body, a mosaic (composite) or other piezoelectric material. In one embodiment, the piezoelectric ceramic comprises off-the-shelf components like those commercially available from CTS of Albuquerque, N. Mex. (e.g., HDD3203). In alternative embodiments, ceramic layers formed by tape casting or other processes are used. Using commercially available piezoelectric provides cost advantages. In yet further alternative embodiments, transducer materials other than piezoelectrics, such as capacitive microelectromechanical ultrasound devices, are used. Different or the same materials may be used for different layers of transducer material.

The layers of transducer material comprise a bottom layer 24, a middle layer 26, and a top layer 28. Each layer 22 comprises a sheet of transducer material. The thickness of each sheet is determined as a function of the total thickness of the transducer element. Where each layer has a same thickness, the total thickness of the transducer element is divided by the number of layers. In alternative embodiments, different layers may have different thicknesses. The thickness may vary as a function of elevation or azimuthal position of the element in the array and/or as a function of azimuthal and/or elevational position within an element for one, a subset or all of the layers 22.

The dimensions of the layers 22 and elements 20 are a function of the transducer design, such as a function of the desired operating frequency, bandwidth, focusing resolution, or other characteristics dependent upon the transducer application. Layers of differing thicknesses and/or shapes may be formed using common tools and techniques known in the art, such as lapping, grinding, dicing, and bonding, reducing costs, increasing adaptability and reducing the time to market. In other alternative embodiments, one or more of the layers 22 is of a non-uniform thickness such as described in U.S. Pat. Nos. 5,438,998 and 5,415,175, the disclosures of which are both incorporated herein by reference. For example, a piano-concave transducer or a transducer with frequency-dependent focusing is used where the array or individual elements have a concave or a convex shape.

Each layer 22 of each element 20 includes a positive electrode 30 and a negative electrode 32 formed on the layer 22. The terms positive and negative electrode refer to the transducer arrays connection with an ultrasound system where the positive electrodes are coupled to signal traces and negative electrodes are coupled to ground traces or vice versa. Positive and negative are intended to reflect opposite poles on the layers in general. Positive and negative electrodes may be reversed in orientation. The negative electrode 32 of the top layer 28 covers a bottom surface, and more preferably a substantial portion of the bottom surface of the top layer 28. The positive electrode 30 covers a top surface, and more preferably an entire top surface, a side surface and a portion of the bottom surface of the top layer 28. Top and bottom, as used herein, refer to the orientation of the layer in the range dimension as shown in the figures. The negative electrode 32 of the middle layer 26 covers the top surface of the layer 26, and more preferably covers a substantial portion of the top surface 26, a side surface and a portion of the bottom surface of the layer 26. The positive electrode 30 of the middle layer 26 covers a bottom surface of the middle layer 26, and more preferably a substantial portion of the bottom surface, a side surface and a portion of the top surface of the middle layer 26. The positive electrode 32 of the bottom layer 24 covers a top surface of the layer 24, and more preferably a substantial portion of the top surface of the layer 24. The negative electrode 32 of the bottom layer 24 covers a bottom surface of the layer 24, and more preferably covers the entire bottom surface, a side surface and a portion of the top surface of the bottom layer 24. In alternative embodiments, electrode material is provided on both side surfaces of one or both of the top and bottom layers 28 and 24. Other electrode arrangements and connections may be used, such as wire bonding, flex circuit connections, or via connections.

The continuous positive and negative electrodes 30 and 32 are sputter deposited and comprise gold. Other metals, such as nickel and silver, and other surfacing techniques may be used. In one embodiment, the electrode has a thickness of about 1,500–3,000 angstroms, but lesser or greater thicknesses may be used.

The positive electrode 30 is separated from the negative electrode 32 on each layer 22 by a discontinuity 34. On the top layer 28, the discontinuity 34 is on a bottom surface and an edge surface. For the middle layer 26, the discontinuities 34 are on the top and bottom surfaces. For the bottom layer 24, the discontinuities 34 are on the top and an edge surface. The discontinuities 34 separate and electrically isolate the positive and negative electrodes 30 and 32. The layers 22 are stacked together so that the discontinuities 34 on the top and bottom surfaces of the layers 22 align. The positive electrodes 30 and the negative electrodes 32 of each element are electrically coupled together, respectively. Each layer 22 of each element 20 substantially has a positive electrode 30 on one surface and a negative electrode 32 on an opposite surface. In alternative embodiments, discontinuities 34 may be provided at different positions, such as providing a discontinuity on a top or bottom surface rather than at a side or on a corner.

The electrodes 30, 32 of each layer 22 contact the electrodes 30, 32 of other layers 22 by asperity contact. Additional soldering, wire bands or via connections are not required, but may be used. The lapping, grinding or other manufacturing processes for the transducer materials provides a fine roughened surface. The roughness of the surface allows for an even distribution of physical and electrical contact between the electrodes 30, 32.

The layers 22 are held together by polymeric bonding. Polymeric bonding compound is applied between each layer 22. As the layers 22 are pressed together, the viscous bonding compound fills gaps and allows asperity contact between the electrodes. In alternative embodiments, other bonding agents may be used, such as associated with anodic bonding, welding or fusing.

The elevationally spaced elements 20 are separated by an air gap 36. By bonding the layers 22 of each element 20, a composite filler is not needed between the elements 20. After assembly, other gases may be used to separate the elements 20. The gas or air may also be used to separate elements in the azimuthal dimension. In alternative embodiments, a liquid, plasma or solid filler material is deposited within the gaps 36. As is discussed below, a method of manufacture of one embodiment provides for the spacing of the elements 20 to allow air or other gases to be used to acoustically and mechanically separate the elements 20.

Various techniques may be used for manufacturing the multiple dimensional multi-layer transducer array. FIGS. 3–5 represent one embodiment for manufacturing multi-layer transducers with an odd number of layers. In the example of FIGS. 3–5, three layers 22 are used, but any add number of layers may be provided. Also as represented by FIGS. 3–5, three elevationally spaced elements are used, but any number of elements may be provided using the techniques discussed below. In the example, one azimuthally spaced row of elevationally spaced elements is created. In alternative embodiments, two or more azimuthally spaced rows are created from the same or different sheets of piezoelectric or transducer material.

Figure 3A:
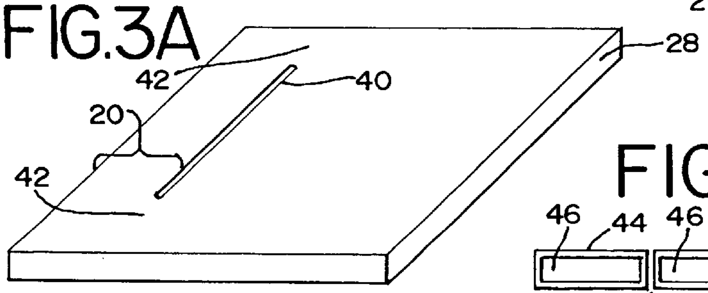
FIGS. 3A–3F, 4A–4D and 5A–5F are perspective and cross-sectional views of first, second, and third layers of the transducer elements shown in FIG. 2 during various stages of manufacture.

FIG. 3A shows the top layer 28. The top layer 28 is plunge cut to form the aperture 40. A dicing saw, etching, laser cut, wire saw or other cutting technique is used to form the aperture 40. The aperture 40 extends along an azimuthal dimension but does not extend across the entire azimuthal width of the top layer 28. In one embodiment, the aperture 40 is centered along the azimuthal width. In other embodiments, the aperture 40 is off-center or extends to one edge. The aperture 40 is positioned along the elevational axis so that one of the elements 20 is defined by the aperture 40 and an edge of the top layer 28. One or more bridges 42 connect the element 20 to the remainder of the top layer 28. As shown in this example, two bridges 42 connect the element 20 the remainder of the top layer 28 after aperture 40 is formed. The plunge cut is preferably made through the entire thickness along the range dimension of the top layer 28.

Figure 3B:
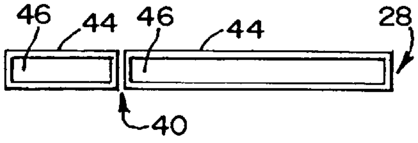

After the aperture 40 is formed, the top layer 28 is metallized. Using sputter deposition, wet chemical plating, vapor deposition or any other method that provides suitable adhesion and thickness control, electrodes 44 as shown in FIG. 3B are formed around all or most surfaces of the transducer material 46 of the top layer 28. In one embodiment, a titanium seed is deposited on the transducer material 46. A thicker layer of gold is then sputter deposited, followed by electroplating for adding additional gold. As shown in the cross-sectional FIG. 3B of FIG. 3A, the electrode 44 covers the edges of the aperture 40.

Figure 3C:
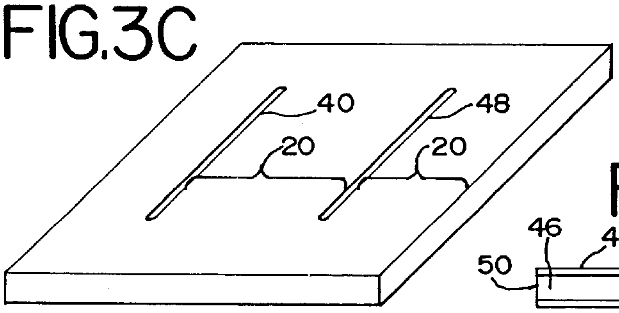
Figure 3D:
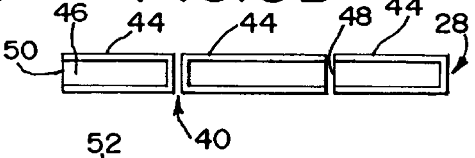

Referring to FIG. 3C, a second plunge cut forms an aperture 48. The aperture 48 is parallel to the aperture 40 and extends only over a portion of the entire azimuthal width of the top layer 28 as discussed above. In alternative embodiments, the apertures 40 and 48 are not parallel. The aperture 48 is also shown in FIG. 3D which is a cross-section of FIG. 3C. The plunge cut results in exposed edges of the transducer material 46 in the aperture 48 (e.g., edges without an electrode 44.) The aperture 48 defines two additional elements 20, the center element and rightmost elements as shown in FIGS. 3C and D.

FIG. 3D also shows the removal of electrode material from a left edge 50 of the top layer 28. The electrode material is removed to expose the edge 50 by sanding, dicing, cutting, laser cutting, cutting with a wire saw or etching.

Figure 3E:
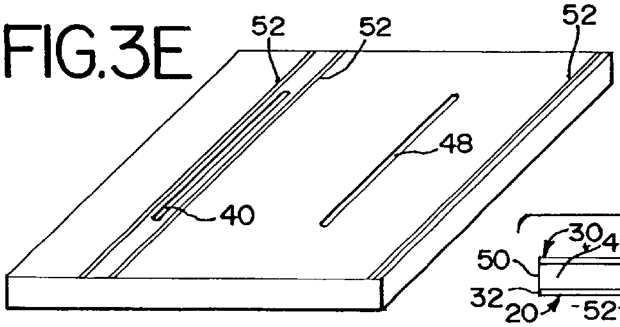

FIG. 3E shows the formation of discontinuities 52 on the electrode 44. The discontinuities 52 are formed by using a dicing saw, patterning the discontinuity during electrode deposition, masking during sputter deposition of the metalization, photolithography or any other method suitable for removing sections of the electrode or selectively preventing the formation of an electrode. The discontinuities 52 electrically isolate sections of the electrode 44. The discontinuities 52 are parallel to the apertures 40 and 48 in one embodiment, but may be at an angle to one or both apertures 40, 48, may curve or have different shapes isolating electrodes.

Figure 3F:
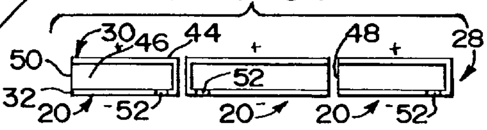

FIG. 3F shows the top layer 28 with the discontinuities 52. Each element 20 has two electrodes 44 defined by exposed surfaces on the transducer material 46. For example, each element 20 includes a positive electrode 30 and a negative electrode 32. The electrodes are separated by discontinuities 52, exposed edge 50, and/or aperture 48. The area of the discontinuities 52 is preferably wide enough to electrically isolate the positive electrodes 30 from the negative electrodes 32. For this top layer 28, the electrodes 44 are formed such that at least a portion of the positive electrode 30 and negative electrode 32 are on a bottom surface. The discontinuities 52 are displaced from an edge by a distance far enough to leave a suitable mating surface of the minority electrode for making electrical contact with a minority electrode on an adjacent layer. The layers 22 will then be arranged so that the contacting electrodes form an integrated electrode with alternating polarity as a function of the range dimension.

The top layer 28 is poled. An electric field, such as a direct current, is applied across the electrodes 44 to align the crystals of the transducer material. In alternative embodiments, poling is performed at a later time or is not performed.

Figure 4A:
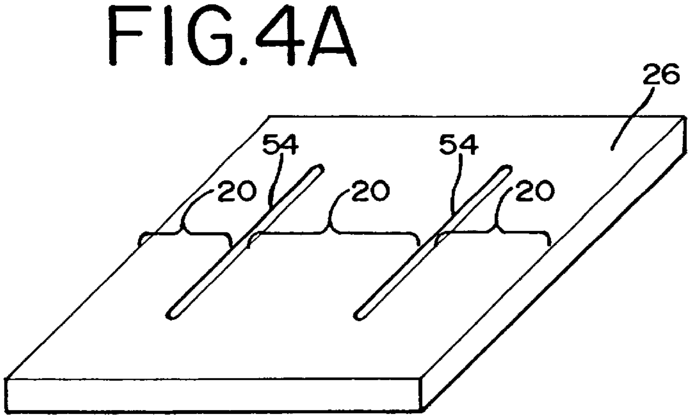
Figure 4B:
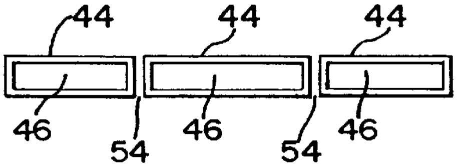

FIG. 4A shows the middle layer 26. Two plunge cuts form apertures 54. Apertures 54 extend along an azimuthal width but not the entire azimuthal width of the middle layer 26. The apertures 54 define the elevationally spaced elements 20. As shown in FIG. 4B, the middle layer 26 is metallized to form the electrodes 44. The electrodes 44 are formed after the apertures 54. The electrodes 44 are deposited on, all or most surfaces of the transducer material 46, including within the apertures 54.

Figure 4C:
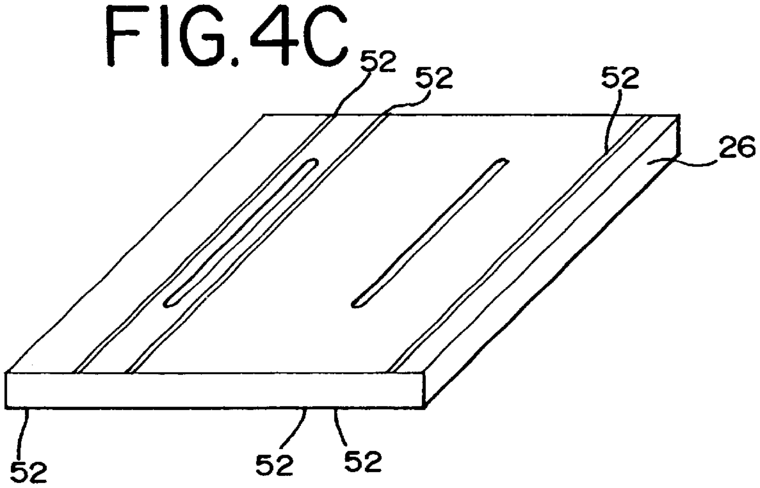
Figure 4D:
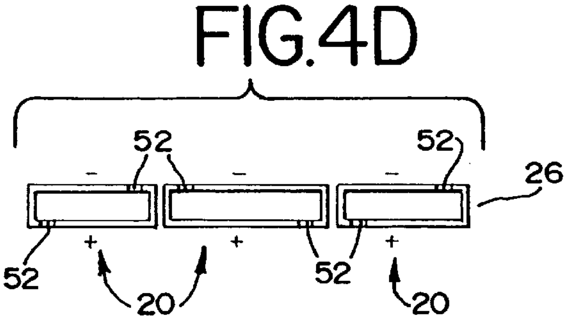

FIGS. 4C and 4D show the formation of discontinuities 52 on the top and bottom surfaces of the middle layer 26. FIG. 4D is a cross-section of FIG. 4C. The discontinuities 52 electrically isolate positive electrodes 32 from negative electrodes 30. Each negative or positive electrode 30 or 32 covers a substantial portion of the upper or lower surface, respectively, of the element 20. The remainder of each surface comprises an electrode 44 associated with a different polarity. The discontinuities 52 are formed such that both the positive and negative electrodes 30 and 32 of the middle layer 26 will contact the electrodes 44 of the top layer 28 and the bottom layer 24.

After formation of the positive and negative electrodes 30 and 32, the middle layer 26 is poled. Alternatively, the middle layer 26 is not poled.

Figure 5A:
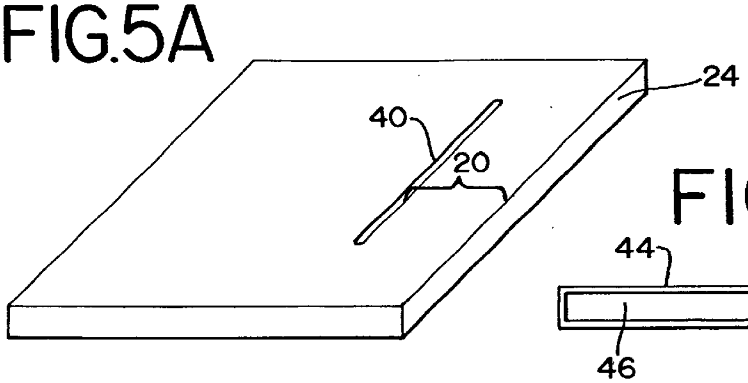

FIG. 5A shows the first step in forming the bottom layer 24. A plunge cut creates aperture 40. The aperture 40 creates one of the elevationally spaced elements 20. For tile 1.5-dimensional transducer array of this example, the element 20 is on a different elevations side than the element 20 defined by the aperture 40 of the top layer 28 (i.e., the plunge cut 40 for the top layer 28 forms the left element 20 and the plunge cut 40 of the bottom layer 24 forms the rightmost element 20).

Figure 5B:
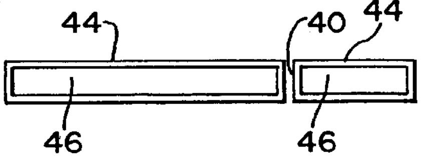
Figure 5C:
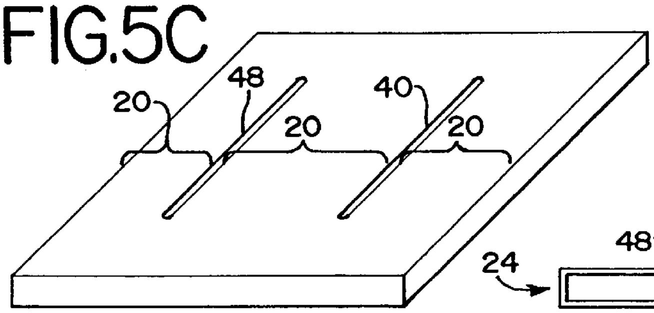
Figure 5D:
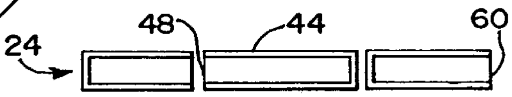

FIG. 5B is a cross-sectional view of FIG. 5A after the bottom layer 24 has been metallized. Electrodes 44 are formed on every exposed edge of the transducer material 46, including within the aperture 40. FIG. 5C shows the formation of another aperture 48 to define two additional elevationally spaced elements 20. The plunge cut to form the aperture 48 exposes transducer material surfaces within the aperture 48 as shown in FIG. 5D. Electrode material 44 does not cover the exposed surfaces within the aperture 48. FIG. 5D also shows the removal of electrode material from a rightmost edge 60 of the bottom layer 24.

Figure 5E:
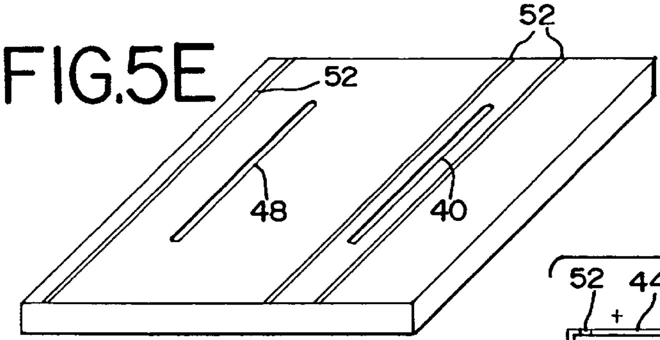
Figure 5F:
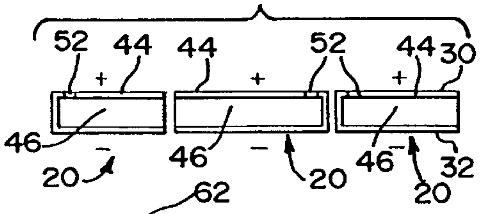

FIG. 5E shows the formation of discontinuities 52 on a top surface of the bottom layer 24. As shown in FIG. 5F, the discontinuities 52, exposed surfaces in the aperture 50 and edge 60 define positive and negative electrodes 30, 32 on each of the elements 20. The positive and negative electrodes 30, 32 are electrically isolated. The transducer material 46 of each element 20 is then poled. Alternatively, no poling is performed or poled at a different time.

The top, middle, and bottom layers 28, 26, 24 are stacked and aligned as shown in FIG. 2. The discontinuities 34, 52 align to form electrically parallel multi-layered piezoelectric elements 20. As shown, the stacked assembly begins with a negative electrode 32 on the bottom of the element 20 and ends with a positive electrode 30 on the top of the element 20. In alternative embodiments, either a positive or negative starting electrode orientation may be used. Preferably, the electrodes 44 are arranged so that electrode polarity is alternating as a function of layer 22 within the element 20.

As stacked, the electrodes 44 contact each other through asperity contact. The asperity contact provides for electrical connection of each positive electrode 30 of each layer 22 to the other positive electrodes of other layers 22. Asperity contact also provides electrical connection for the negative electrodes 32.

The apertures 36 are used to align the layers 22. A bar, rod or other device is inserted within one or more of the apertures 36 to align the various layers 22. In alternative embodiments, other alignment techniques may be used, such as stacking in a mold, external mechanical alignment or the additional manufacturing techniques discussed below.

After alignment, the asperity contact is maintained by polymeric bonding. An epoxy bond or other adhesive providing adequate joint strength with enough viscosity to allow point to point or asperity contact of the adjacent electrodes 44 is used. For example, an epoxy adhesive, such as EPO-TEC 301, is used.

Figure 6:
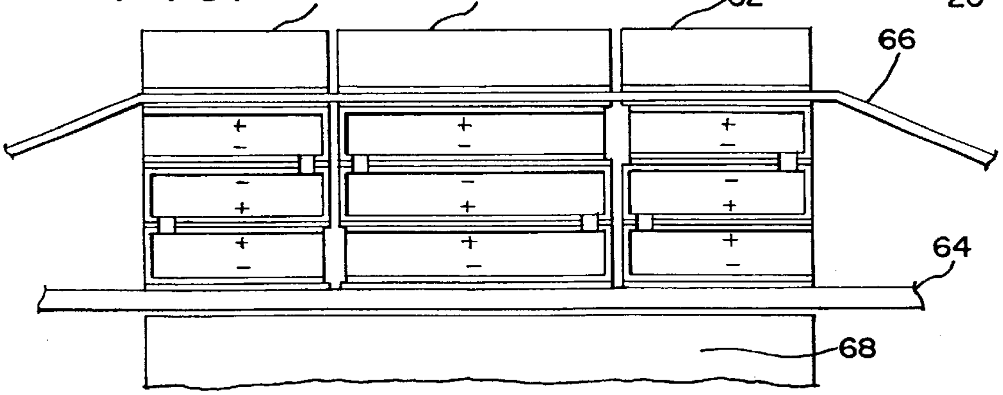
FIG. 6 is a cross-sectional view of the multi-layer transducer elements of FIG. 2 used in an assembled transducer in one embodiment.
Figure 7:
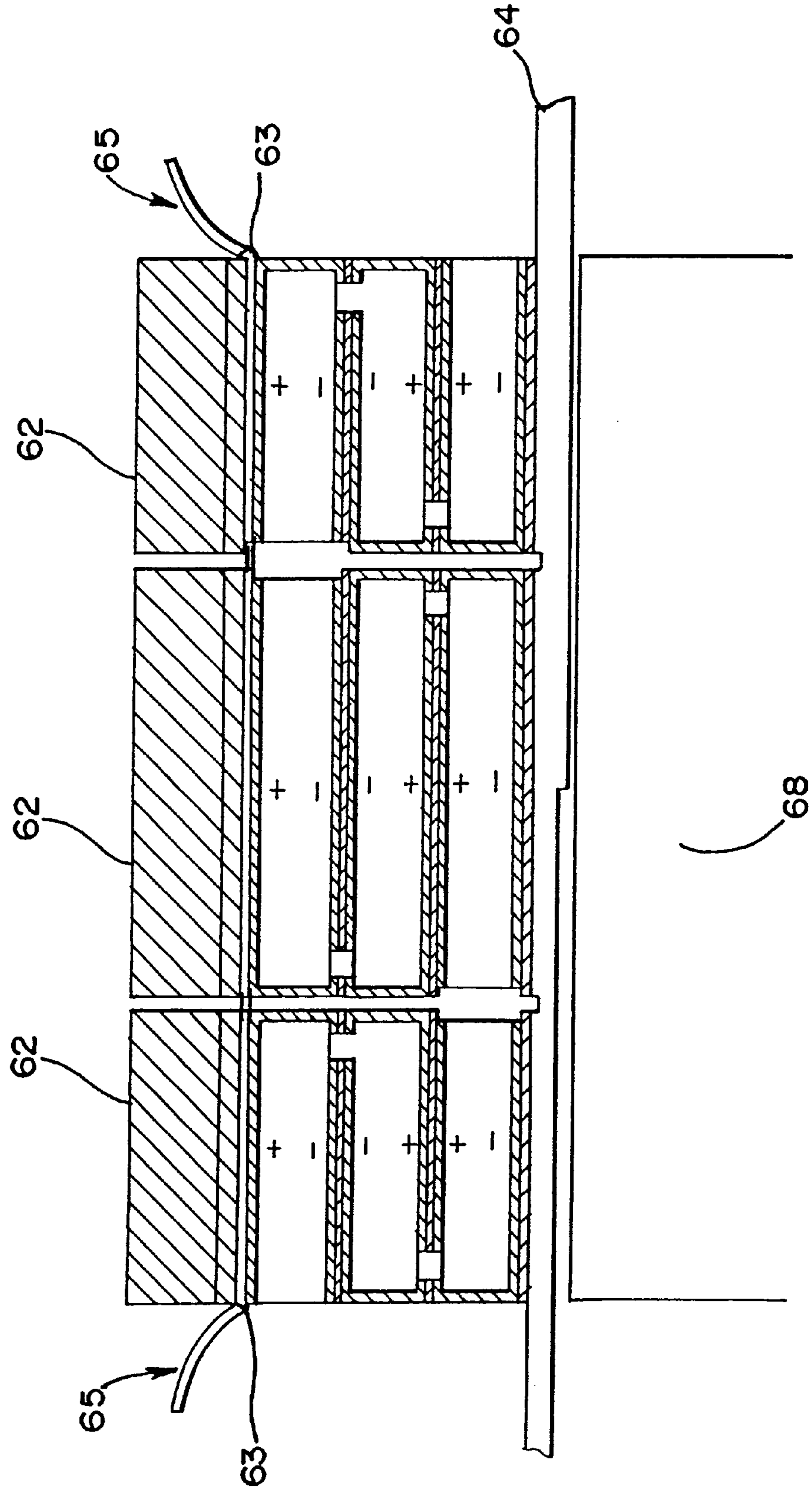
FIG. 7 is a cross-sectional view of the multi-layer transducers shown in FIG. 2 used in an assembled transducer in another embodiment.

The transducer is assembled from the multi-layer transducer material. As shown in FIGS. 6 and 7, a matching layer 62 is cut along an azimuthal width, either the entire width or a portion of the width, and placed on top of the stack of layers 22. A matching layer 62 comprises any of various materials for acoustically matching the transducer material 46 to a body or gel. The matching layer 62 is shaped so as to be of a similar azimuthal and elevational dimension as each element 20. The matching layer 62 may vary in thickness, in diameter or acoustic properties and/or comprise one or more layers. The matching layer 62 is bonded to the stacked layers of transducer material.

A bottom of the stacked layers 22 is coupled with a signal and ground flex circuit 64. In one embodiment, the flex circuit 64 has a center pad area formed of a thin layer of copper deposited on a polyamide film, such as KAPTON™, commercially available from E.I. DuPont Company. Individual traces extend from each side of the center pad area. The flex circuits 64 are bonded to the stacked layers of transducer material with an epoxy adhesive or other bonding agent. The flex circuit 64 provides electrical contact with the electrodes 44 of the stacked transducer material through asperity contact. The polymeric bond maintains the contact between the flexible circuit 64 and the electrodes 44. The flexible circuit 64 is laid out such that individual signal lines connect the middle and outer elements 20 to discrete signal lines. In alternative embodiments, the elements 20 are shorted together. In yet other alternative embodiments, the flexible circuit 64 is coupled with a top surface of the stacked layers 22.

Different techniques may be used for connecting the positive electrodes 30 of the stacked layers of transducer material to the ultrasound system. In one embodiment shown in FIG. 6, foil 66 or another electrically conducting substance is positioned across the top layer 28 in contact with the positive electrodes 30. The foil 66 is bonded, such as polymeric bonding or other adhesion, to the matching layer 62 and to the top layer 28. Asperity contact provides electrical contact between the foil 66 and the positive electrodes 32 of each element 20. The foil 66 connects to an electrical ground.

In an alternative embodiment shown in FIG. 7, the matching layer 62 is metallized, such as by using sputter deposition, forming an electrode 63 on at least the lower surface of the matching layer 62. A ground bus 65, such as metallized Mylar film or other electrically conductive substance, is connected to the electrodes formed on the matching layer 62. The matching layer 22 may comprise conductive material.

The flex circuit 64 and stacked layers 22 are further bonded to an acoustic backing material 68. The acoustic backing material 68 comprises mechanical support for the array and has acoustic properties for desired performance.

During assembly, the bridges 42 in conjunction with the apertures 36 hold each layer 22 and associated element 20 in position. The elements 20 are then mechanically or acoustically isolated from each other by removing the bridges 42. The bridges are diced along the elevation dimension to separate the elements 20. For example, the layers 22 are diced along a line perpendicular to the longest dimension of the apertures 36, 40, 54, 48. The dicing intersects the edges of the apertures 40, 48, 54, acoustically isolating each element. The cut is made through all of the layers 22.

The acoustically isolated elements 20 are separated by air or gas. In alternative embodiments, a polymer or epoxy filler is inserted between the elevationally and azimuthally spaced elements 20. After acoustically isolating each element 20, a plurality of elevationally spaced elements 20 are aligned along the azimuthal dimension to define the array.

The above described embodiments may be used with the processes, structures or materials described in U.S. Pat. No. 6,121,718, the disclosure of which is incorporated herein by reference. The single dimension transducer array of this patent is manufactured as a multiple dimensional array.

II. Array with an Even Number of Layers Having Asperity Contact

In one embodiment, arrays of elements with an even number of layers are provided. The layers of transducer material are polymericly bonded and electrically connected through asperity contact. Two layer elements may be used for low and middle ultrasound frequency acoustic transmissions, such as 5 MHz. For the two layer example, thicker piezoelectric layers than for a three layer element operating at the same frequency may be used. Four or more layers may also be provided. Asperity contact provides a minimal bondline between the layers of transducer material, improving performance and extending the frequency of operation.

In one embodiment, the arrays comprise a one dimensional array of elements in a single row along the azimuthal dimension. For example, the multi-layer transducers with an odd number of layers disclosed in U.S. Pat. No. 6,121,718 are provided with an even number of layers. Alternatively, a multi-dimensional array with elements having an even number of layers is provided. For example, the manufacturing processes discussed above for the multi-dimensional, multi-layer arrays may be used with an even number of layers. Positive and negative electrodes connect with asperity contact and are separated by discontinuities. For arrays of any dimension, the various processes, materials and structures discussed above, including alternatives, may be used with an even number of layers as discussed below.

Figure 8:
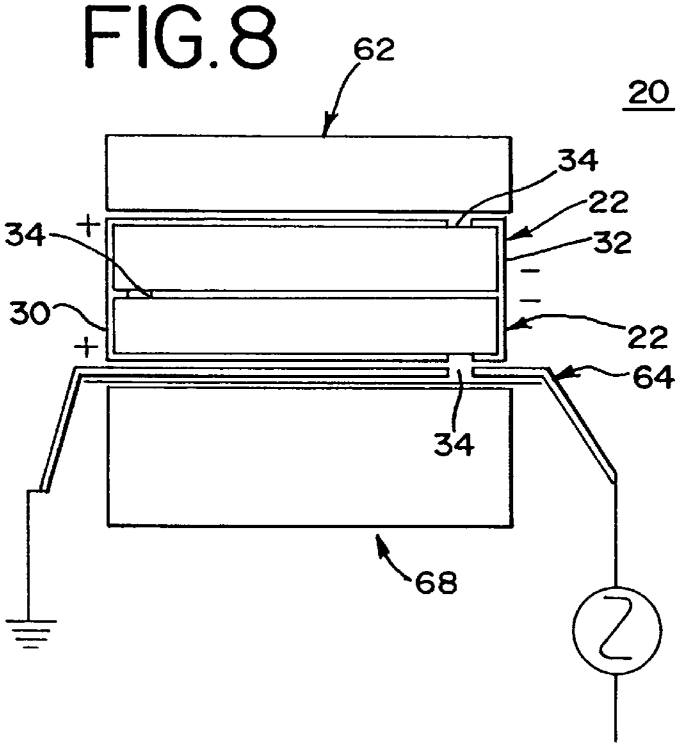
FIG. 8 is a cross-sectional view along the elevation and range dimensions of one embodiment of a multi-layered transducer element.
Figure 9:
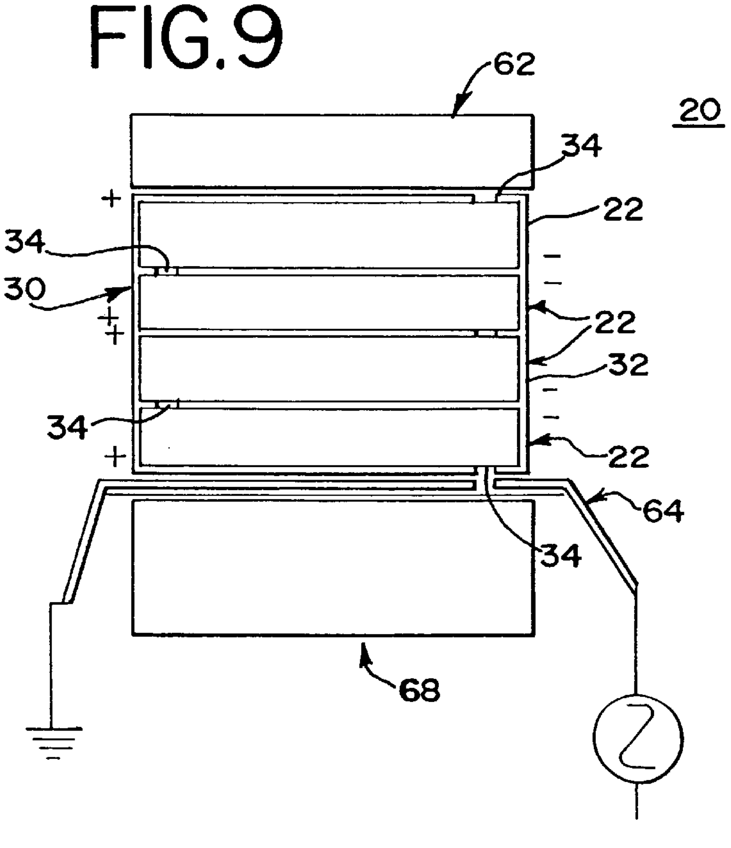
FIG. 9 is a cross-sectional view along the elevation and range dimensions of another embodiment of multi-layered transducer element.

FIGS. 8 and 9 show cross-sections of transducer elements 20 comprising two and four layers 22 of transducer material, respectively. Alternatively, six or more layers may be provided. The elements 20 also include positive electrodes 30 and negative electrodes 32, matching layers 62, acoustic backing material 68 and flex circuits 64. Additional, fewer or different components maybe be used.

The positive and negative electrodes 30, 32 are separated by discontinuities 34. As shown, the discontinuities 34 are on top and bottom surfaces of the layers 22 relative to the direction of acoustic propagation (i.e. top and bottom along the range axis). In alternative embodiments, one or more of the discontinuities 34 are located at a corner or along an edge (i.e. side) surface.

The discontinuities 34 of adjacent surfaces of adjacent layers 22 are aligned. The positive electrodes 30 and negative electrodes 32 of each layer contact associated positive and negative electrodes 30, 32 of adjacent layers. The contact comprises an asperity contact, but other electrical connections may be provided.

Figure 10A:
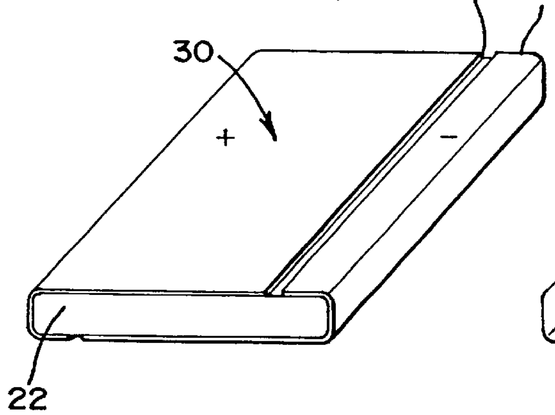
FIGS. 10A–D are perspective views with top and bottom orientations of each of the two layers of FIG. 8 or each of pairs of layers 22 of FIG. 9.
Figure 10C:
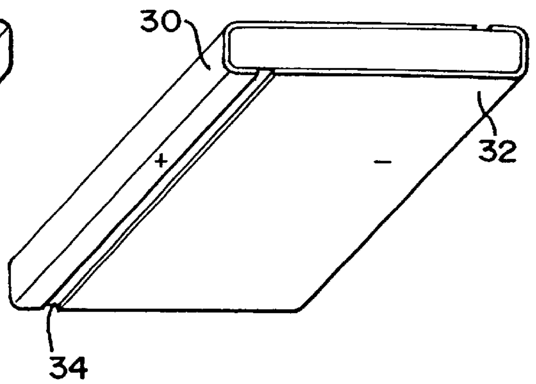
Figure 10B:
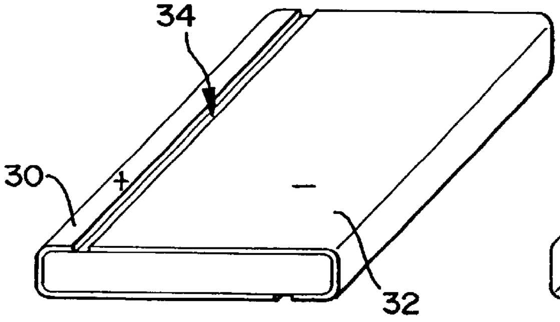
Figure 10D:
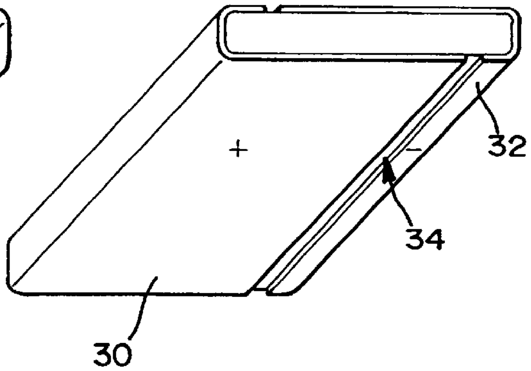

FIGS. 10A–D show top and bottom perspective views of each of the two layers of FIG. 8 or each of pairs of layers 22 of FIG. 9. FIGS. 10A and 10C show top and bottom views of a first or top layer 22. FIGS. 10B and 10D show top and bottom views of a second or bottom layer 22. The discontinuities 34 for the bottom surface of the top layer 22 and the top surface of the bottom layer 22 are positioned to align when the layers are stacked. The negative electrode 32 of the top layer 22 contacts the negative electrode 32 of the bottom layer 22 when the layers are stacked. The positive electrodes 30 of the top and bottom layers 22 contact when the layers are stacked. Each layer 22 comprises two discontinuities 34. In one embodiment, the electrodes 30, 32 and discontinuities 34 of the two layers 22 are substantially the same, such as mirror images, for efficient manufacturing. In alternative embodiments, the layers 22 are asymmetrical.

Figure 11:
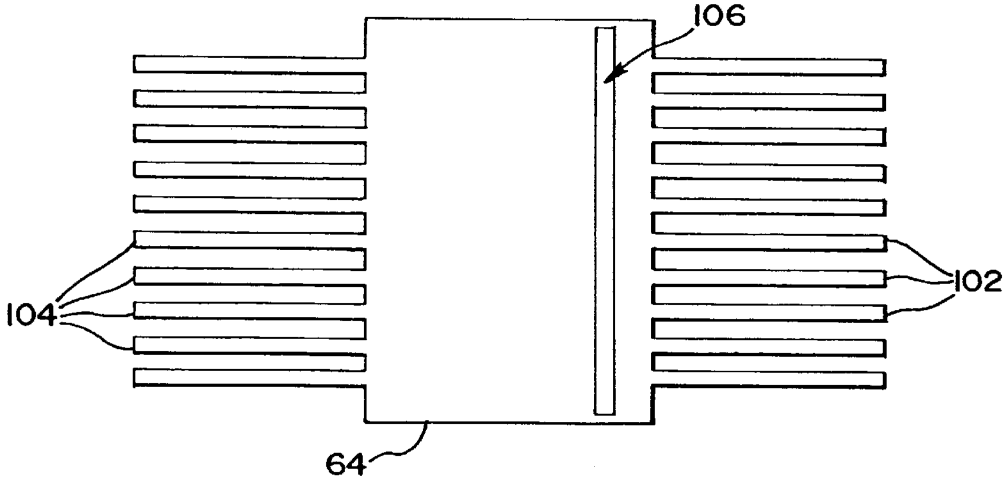
FIG. 11 is a top view of a flex circuit according to one embodiment.

The layers 22 are bonded or connected together as discussed above and shown in FIGS. 8 and 9. The layers 22 of transducer material are also bonded or attached to the flex circuit 64. The thin, flexible printed flex circuit 64 interconnects the positive and negative electrodes 30, 32 of each element 20 of an array of elements 20 to the ultrasound system with asperity contact. FIG. 11 shows a top view of one embodiment of the flex circuit 64 for use with a one-dimensional array of elements. The flex circuit 64 includes a first plurality of signal traces 102 for electrically connecting the negative electrodes to ground or the ultrasound system and a second plurality of signal traces 104 for electrically connecting the positive electrodes to the ultrasound system. An isolation section 106 is provided for alignment with the discontinuity 34 on the bottom surface of the bottom layer 22. The electrical isolation between elements 20 is created when the elements are azimuthally diced. Alternatively, the flex circuit 64 includes additional isolation sections separating the signal traces 102, 104 for each element 20. In yet another alternative discussed below, the negative signal traces 102 are connected to a top surface of the top layer 22, allowing a larger area of contact.

III. Substantially Similar Configuration of Layers

In one embodiment for one dimensional or multi-dimensional arrays of elements, each layer has a same configuration of two electrodes and two discontinuities. The top and bottom surfaces of each layer of transducer material includes a minority and a majority electrode. The same processing forms each layer. Alternatively, different processing is used to form one or more layers. The layers are stacked. To add an additional layer, another layer with a substantially same configuration is added. By flipping the symmetric layers relative to an adjacent layer, the minority and majority electrodes are aligned for bonding. An even or odd number of layers are provided.

Figures 12A, 12B, 12C, 12D, 12E:
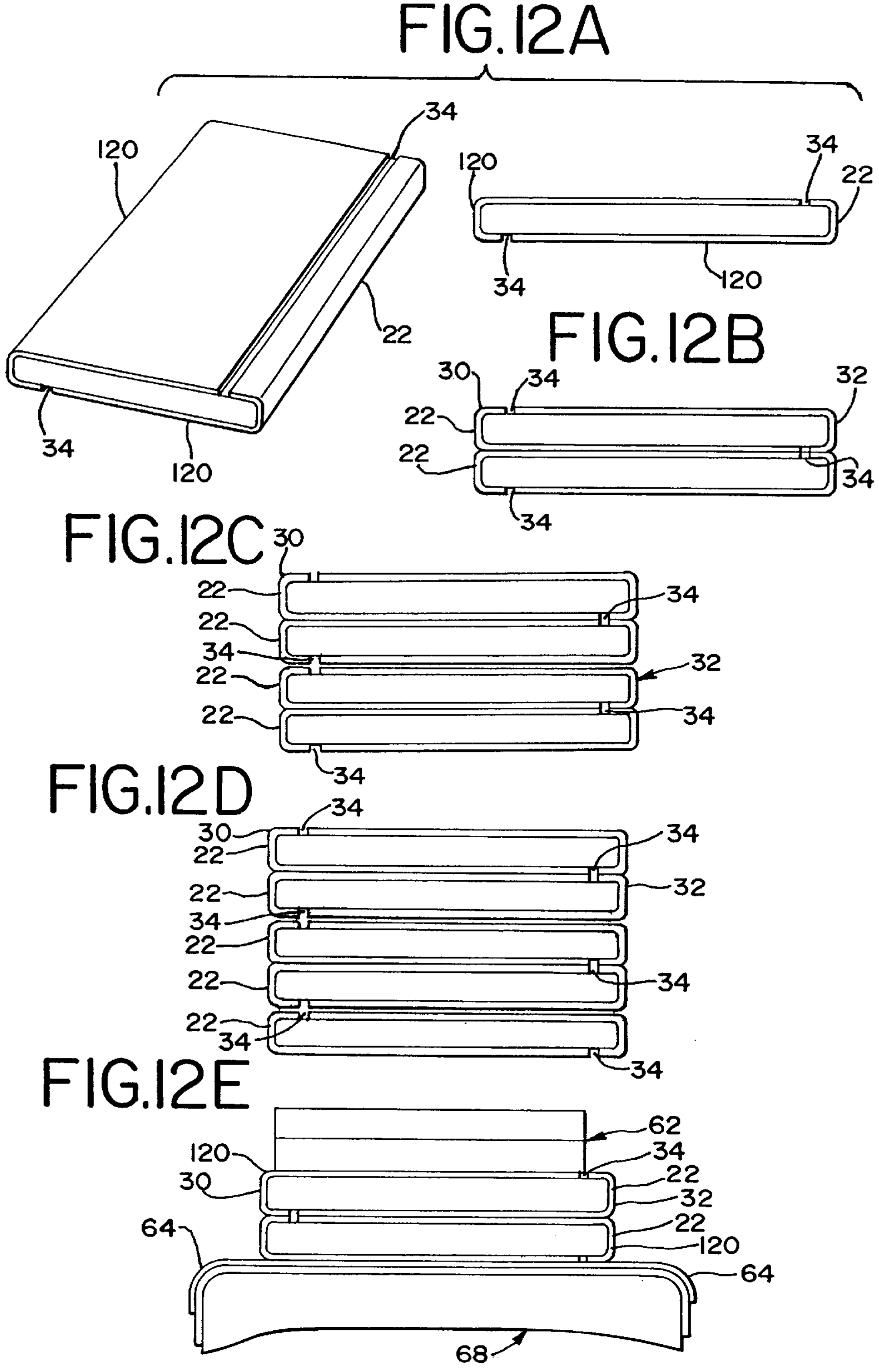
FIG. 12*a* is a perspective view and a cross section view of one embodiment of a layer of a transducer element.
FIGS. 12*b–d* are cross section views of various embodiments of stacked layers of a transducer element.
FIG. 12*e* is a cross section of a multi-layered transducer element according to one embodiment.

FIG. 12*a* shows the configuration of each layer 22. Each layer 22 is individually processed in a substantially same manner. Two discontinuities 34 electrically isolate two electrodes 120. Each electrode 120 is positioned on the top, bottom and a side surface. The discontinuities 34 are positioned to provide a minority and majority electrode on each of the top and bottom surfaces. The discontinuity 34 extends along the length of the azimuth dimension of the layer 22. The position of the discontinuities 34 on the top and bottom surfaces is space a same distance away from opposite edges, providing symmetrical layers 22. In alternative embodiments, the layer 22 is asymmetrical, such as asymmetrical in the elevation dimension.

Two layers 22 are aligned as shown in FIG. 12*b*. By flipping one layer 22 about the elevation axis, two minority and majority electrodes 120 and two discontinuities 34 are aligned. The minority and majority electrodes 120 electrically connect by asperity contact. The discontinuities 34 isolate the electrodes. As aligned, the layers 22 provide two isolated electrodes 120.

FIG. 12*c* shows stacking an additional pair of aligned layers 22. The discontinuities 34 and electrodes 120 are aligned on a bottom surface of one pair and a top surface of another pair. Any number of pairs of layers 22 may be stacked.

FIG. 12*d* shows stacking an additional single layer 22 onto four layers 22 (two pairs), providing five layers 22. The discontinuities 34 and electrodes 120 are aligned on a bottom surface of one layer 22 and a top surface of another layer 22. The odd layers 22 are mirror images or flipped relative to the even layers 22. In alternative embodiments, three or seven or more layers 22 may be provided.

FIG. 12*e* shows a cross section of an element 20 with two layers 22, but additional layers 22 may be provided. The element 20 is positioned in a one-dimensional transducer array, but a multi-dimensional array may be used. An odd number of layers may be provided as shown in FIG. 12*d*. FIG. 12*d* shows five layers 22, but three or seven or more layers may be provided.

As shown in FIG. 12*e*, the flex circuit 64 is bonded or electrically connected with the electrodes 120 to form positive and negative electrodes 30 and 32. A signal trace of the flex circuit 64 connects with one of the majority and minority electrodes 120 on one planar surface, such as a bottom surface of a bottom layer 22 or a top surface of a top layer 22. To allow better acoustic performance, the flex circuit 64 comprises thin multi-layer circuitry with small circuit geometry. In alternative embodiments as discussed below, positive and negative connections may be provided on different or opposite portions of the stacked layers 22.

Asperity contact between the layers 22 and the flex circuit 64 provides electrical connection for positive and negative electrodes 30, 32 for each layer 22. In alternative embodiments, soldering, bonding conductive material, wire bonding or similar electrical attachments provide electrical connection between electrodes 120 and/or the flex circuit 64.

After assembly, the stacked layers 22 are diced or cut to isolate azimuthally spaced elements 20. A one dimensional array of elements 20 is provided.

Figures 13, 14A, 14B, 14C, 14D, 14E:
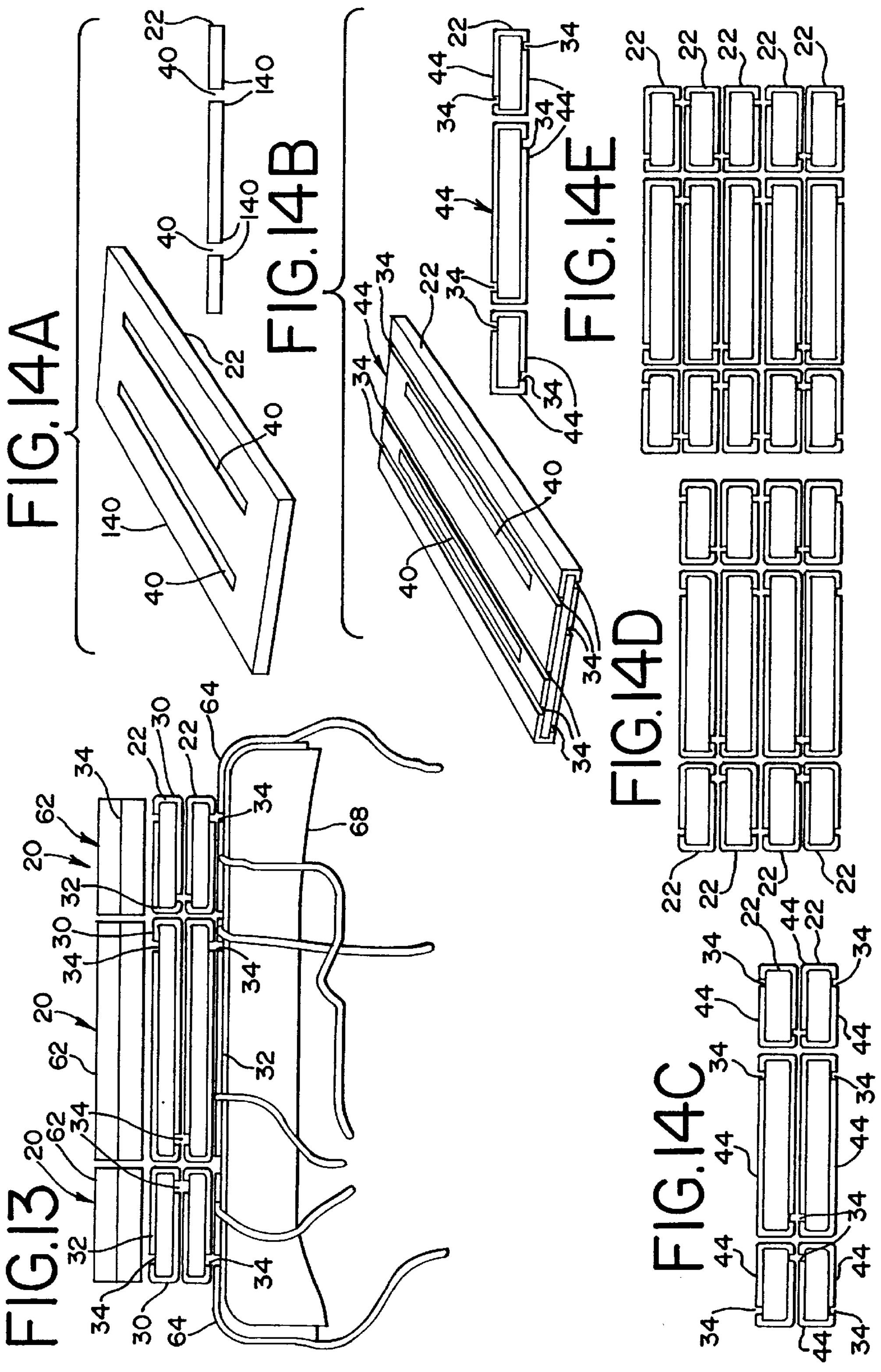
FIG. 13 is a cross section of one embodiment of a multi-layered multidimensional transducer array.
FIGS. 14*a* and *b* are perspective and cross section views of one embodiment of a layer for an element.
FIGS. 14*c–e* are cross section views of stacked layers for one embodiment of a transducer element.

FIG. 13 shows a cross section of a multiple dimension array of elements 20 in a 1.5D array structure. Different elevation element sizes and shapes may be provided. As shown, an even number of layers 22 is provided. In alternative embodiments, an odd number of layers 22 is provided.

Each layer 22 comprises a substantially same configuration of discontinuities 34 and negative and positive electrodes 30, 32 in the range and azimuth plane. For each layer 22 of each element 20, minority and majority electrodes are provided on both top and bottom surfaces. The discontinuities 34 of one layer 22 are aligned with an adjacent layer 22, such as flipping a symmetrical layer 22 or mirror layer 22.

The flex circuit 64 includes a plurality of isolations associated with discontinuities 34 between negative and positive electrodes 30, 32. Separate signal traces are connected to each element 20. The common or separate negative or ground traces may be connected to each element 20.

FIGS. 14*a–e* represent the manufacture of layers 22 with a substantially same configuration for a multi-dimensional array. Each layer 22 is processed individually but in a similar or same manner. Various alternative processes, structures and materials are provided in the discussion above relating to FIGS. 3–5 and are applicable but not repeated here.

FIG. 14*a* shows perspective and cross section views of a layer 22 for a multi-dimensional array. The transducer material 140 is plunge cut to form two apertures 40.

The layer 22 is metalized on a top, two edges and bottom surface, forming the electrode 44. In alternative embodiments, another two edges or all surfaces are also metalized. As shown in the perspective and cross section views of FIG. 14*b*, discontinuities 34 are formed in the electrode 44. Two discontinuities 34 for each section of the layer 22 associated with an element 20 isolate two electrodes 44. One discontinuity 34 for each element 20 is on a top surface and another discontinuity 34 for each element 20 is on a bottom surface, forming a minority and majority electrode for each element 20 on both the top and bottom surfaces.

FIG. 14*c* shows two stacked layers 22. The discontinuities 34 of a top surface of one layer 22 and a bottom surface of another layer 22 are aligned. The minority and majority electrodes 44 on the surfaces also align. The electrodes 44 electrically connect with asperity contact, forming two isolated electrodes 44 for each element 20. Each layer 22 of each element 20 contacts two different electrodes 44.

FIG. 14*d* shows four stacked layers 22 where the layers 22 have a substantially same configuration. FIG. 14*e* shows five stacked layers 22. Other numbers of even or odd layers 22 may be provided. The layers 22 are stacked as discussed above for FIGS. 12*b–d*.

IV. Opposite Polarity Connections on Opposite Surfaces

Figure 15:
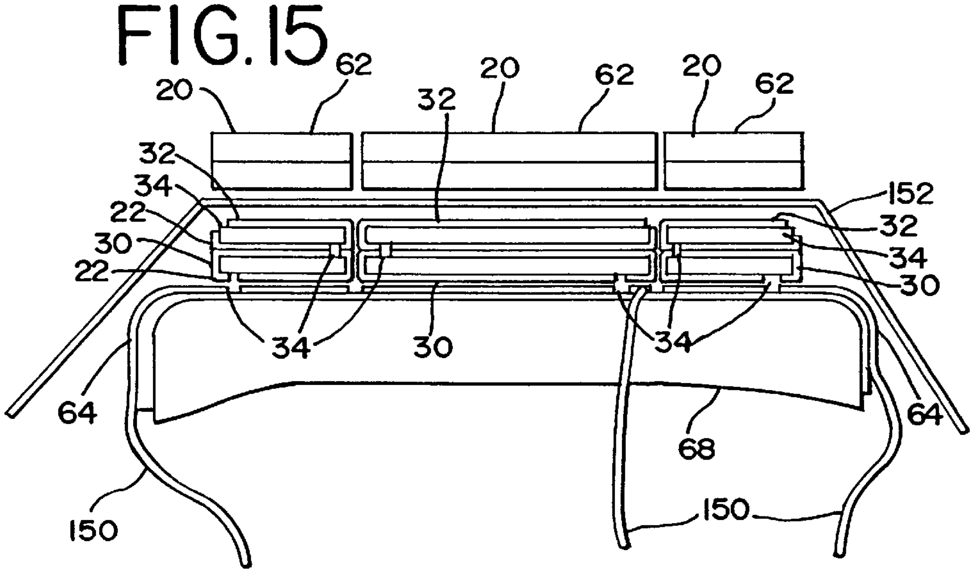
FIG. 15 is a cross section of one embodiment of a multi-layered multi-dimensional transducer array with opposite polarity opposite surface connections.

FIGS. 6 and 15 show alternative embodiments to connecting the flex circuit 64 with the majority and minority electrodes on one surface. These alternate embodiments may be used with any of the elements and/or processes discussed above. Referring to FIG. 15, signal traces 150 connect with the positive electrodes 30 on one surface and ground traces 152 connect with the negative electrodes 32 on a different surface. As shown, the signal traces 150 connect on a bottom surface adjacent to the backing block 68, and the ground traces 152 connect on a top surface adjacent to the acoustic matching layer 62. In alternative embodiments, some or all of the signal or ground traces 150, 152 connect at different places, such as different surfaces or the edges of the layers 22.

The signal and ground traces 150, 152 comprises flex circuits or other alternative electrical connections discussed herein. In one embodiment, the ground traces 152 comprise a flex circuit or foil without isolation sections.

Where the ground or signal traces 152, 150 do not include isolation sections, the discontinuities 34 are positioned at a corner or edge of the layer. For example, FIG. 15 shows the ground traces 152 without isolation sections. The discontinuities 34 on the top surface of the top layer 22 adjacent to the ground trace 152 are formed on the corner edges of the layer 22. The remaining layers 22 are processed or formed as discussed above. For an example of an odd number of layers 22 with opposite pole, opposite surface connection to the ultrasound system, see U.S. Pat. No. 6,121,718.

Figure 16A:
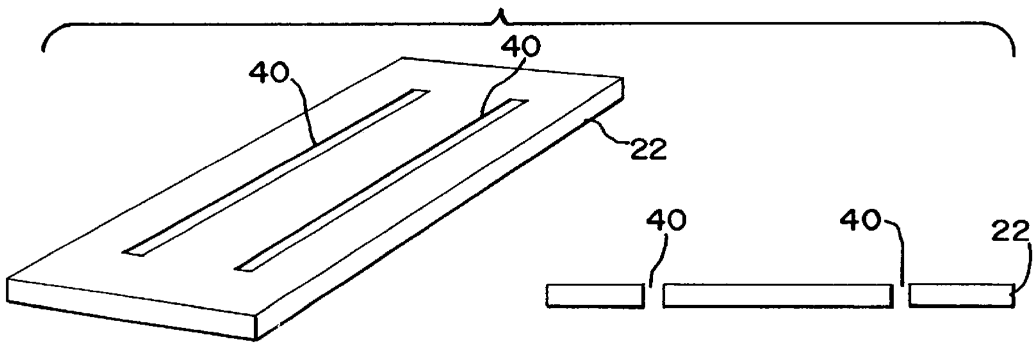
FIGS. 16*a* and *b* are perspective and cross section views of one embodiment of a top layer of the transducer array of FIG. 15.

FIGS. 16*a* and *b* show the formation of the electrode configuration of the top layer 22. In alternative embodiments, FIGS. 16*a* and *b* represent the formation of the bottom or both top and bottom layers 22. Various alternative processes, structures and materials are provided in the discussion above relating to FIGS. 3–5 and are applicable but not repeated here.

Figure 16B:
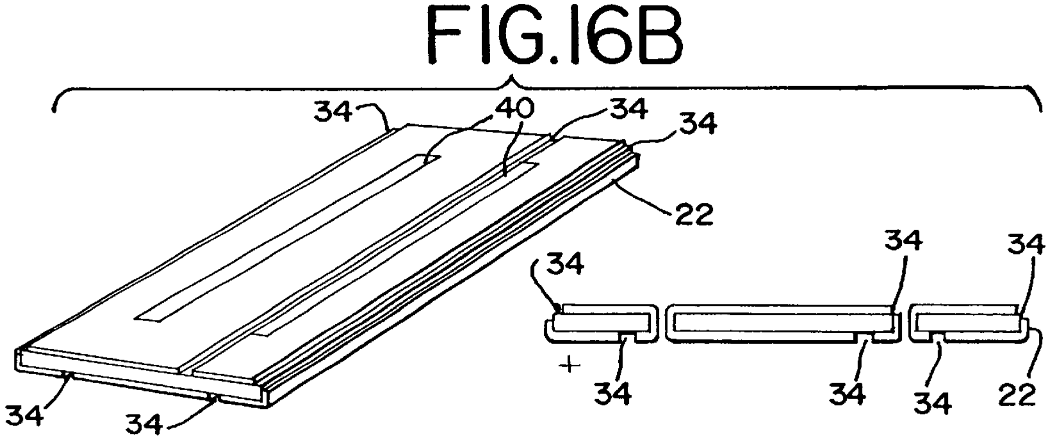

In FIG. 16*a*, plunge cuts form the two apertures 40 in the top layer 22. The layer 22 is metalized, providing an electrode around a portion or the entire layer 22. Discontinuities 34 are formed in the electrodes to isolate two electrodes for each element 20 as shown in FIG. 16*b*. The discontinuities 34 on the bottom surface provide majority and minority electrodes on the planar surface. The discontinuities 34 on the top surface provide one electrode exposed on the surface. For example, the top surface discontinuities 34 are provided on a corner edge or the edge of the layer 22.

Figure 17:
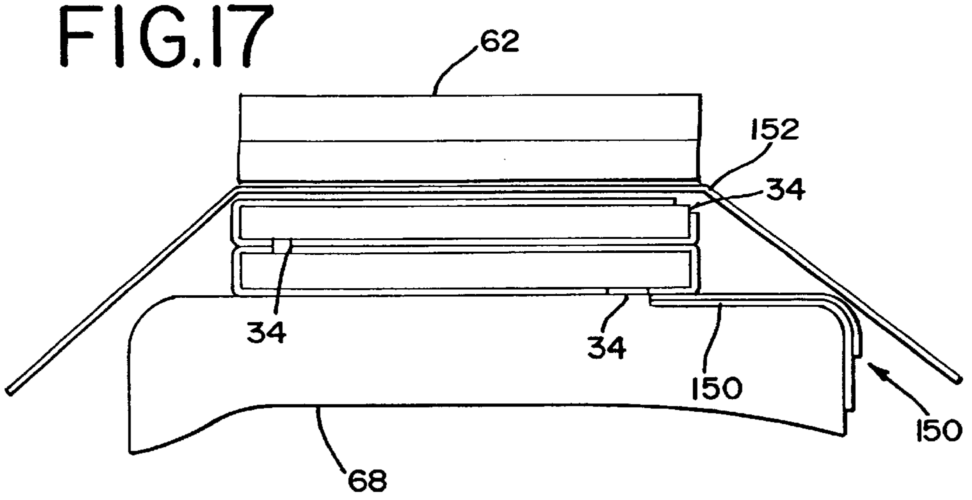
FIG. 17 is a cross section of one embodiment of a multi-layered transducer array with opposite polarity opposite surface connections.

The opposite pole, opposite surface electrical connection to the ultrasound system may be used with multi-dimensional transducer arrays as shown in FIGS. 15 one dimensional transducer arrays as shown in FIG. 17. Full planar electrical connection is provided by isolating the electrodes on a corner or edge. The surface for full planar interconnect has a single electrode. Electrical continuity is provided between layers by asperity contact between minority and majority electrodes on adjacent planar surfaces of adjacent layers 22.

V. Isolating Electrodes After Bonding

In another alternative manufacturing process, the electrodes for a plurality of layers 22 may be created after bonding the layers together. Isolating electrodes after bonding the layers is used on two or three layer elements, but may be used for a larger number of layers. For example, two or three layers are bonded and then electrodes are isolated. Then, the layers are stacked with other layers. As another example, four or more layers are bonded where one or more layers have discontinuities formed before bonding, but at least one layer has discontinuities formed after bonding. For two or three layer elements, all of the discontinuities may be created after bonding the layers together.

Figure 18A:
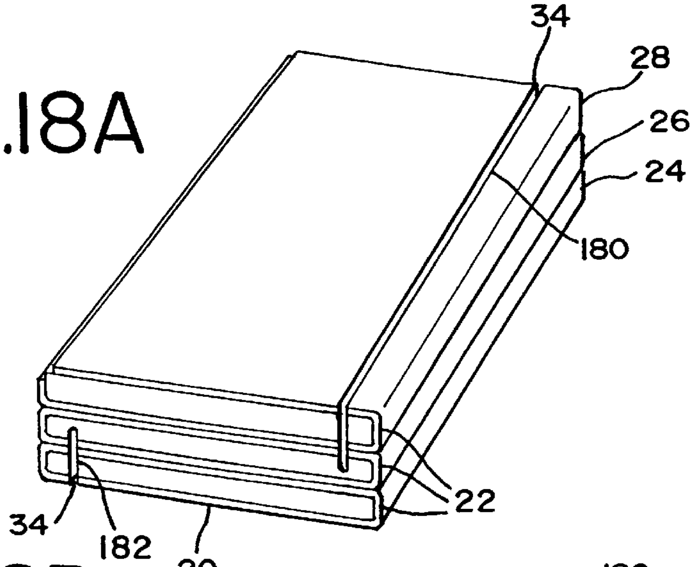
FIGS. 18*a* and *b* are a perspective and a cross section view of one embodiment of a three layer element with kerfs formed after bonding.

FIGS. 18*a* and *b* show a transducer element 20 with three layers 22. For the top layer 28, the discontinuities 34 are formed by a kerf 180 through the top layer 28 and on a corner as discussed above. In alternative embodiments, the second discontinuity 34 is formed on an edge or on the top surface. For the bottom layer 24, the discontinuities 34 are formed by a kerf 182 through the bottom layer 24 and on the bottom surface. In alternative embodiments, the second discontinuity 34 is formed on a corner or edge. For the middle layer, the discontinuities are formed by the kerfs 180 and 182.

The kerfs 180 and 182 extend through one layer 22 and at least through the electrode of an adjacent layer 22. As shown, each kerf 180, 182 forms two discontinuities 34 on one layer 22 and another discontinuity 34 on another layer 22.

Figure 18B:
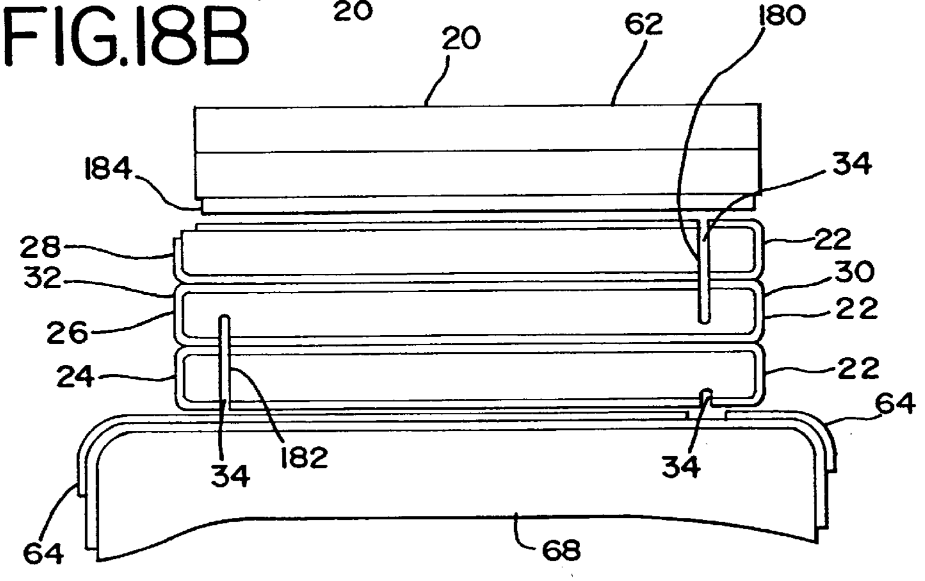

FIG. 18*b* shows the three layers 22 in an assembled element 20. The positive (signal) and negative (ground) electrodes 30 and 32 are formed as two continuous electrodes for the layers 22. Each layer 22 has a majority electrode, a minority electrode and a discontinuity 34 aligned with an adjacent layer 22. The minority and majority electrodes of adjacent layers 22 connect by asperity contact. Alternatively, the electrodes are wire bonded or otherwise electrically connected.

A jumper 184 electrically connects across the kerf 180 on the top surface of the top layer 28. The jumper 184 comprises a layer of foil, a conductive film, a wire jumper, a flex circuit, a bonded electrically conducting material or other electrical connection component. The jumper 184 conducts the positive signal from the flex circuit 64 to form a majority electrode for the top layer 28. In alternative embodiments, the jumper 184 comprises a flex circuit or foil connected to ground or a negative signal trace and the flex circuit 64 carrying the positive signal connects to a different electrode.

The flex circuit 64 carrying the negative or ground signal electrically connects one minority electrode to a majority electrode on the bottom surface of the bottom layer 24. Another discontinuity 34 isolates the positive and negative electrodes 30, 32 on the bottom surface of the bottom layer 22.

Figure 19A:
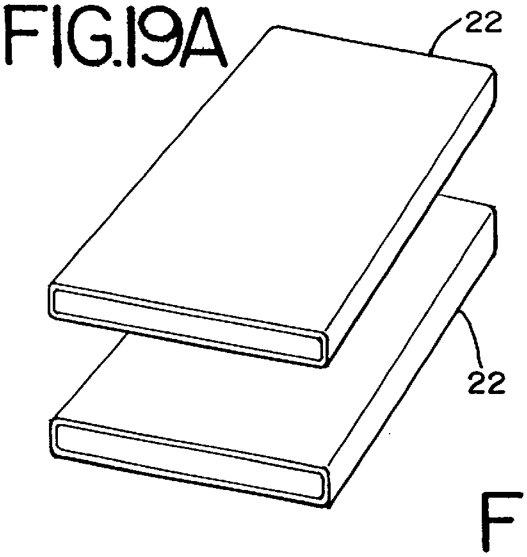
FIGS. 19*a–e* are perspective and cross section views of another embodiment of a multi-layer transducer element with kerfs formed after bonding.
Figure 19B:
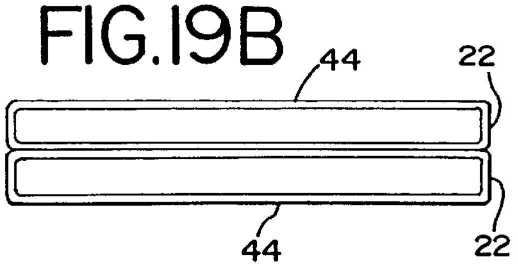
Figure 19C:
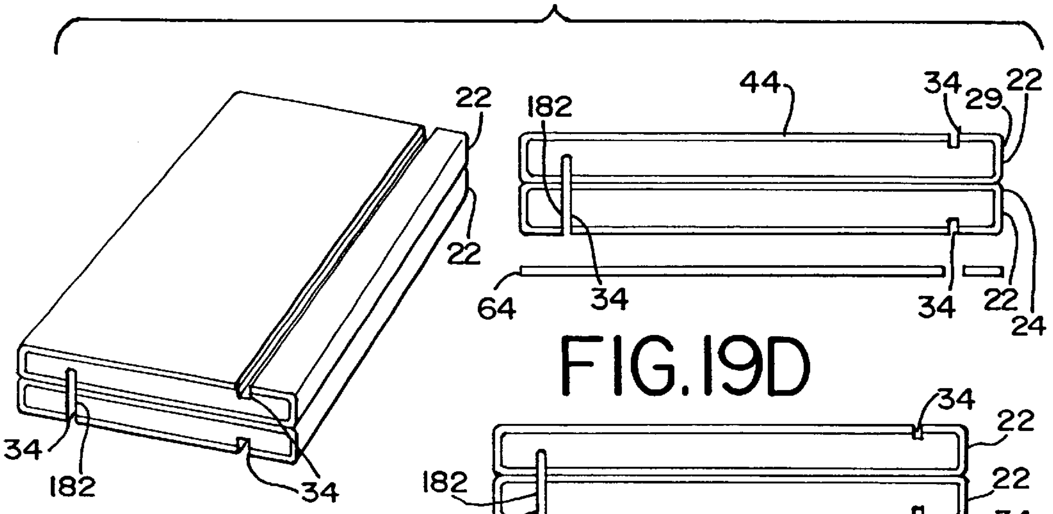

FIGS. 19*a–c* show the layers 22 at different times during the manufacturing process for forming discontinuities after bonding the layers 22. A two layer embodiment is discussed, but other numbers of layers may be provided.

FIG. 19*a* shows two layers 22 each comprising transducer material substantially covered by an electrode 44. A continuous conductive film (the electrode 44) surrounds the transducer material of each layer 22 as shown in FIG. 19*b*.

After the layers 22 are metalized with the conductive film, the layers 22 are bonded together as shown in FIG. 19*b* and discussed above. The electrodes 44 of each layer 22 are in asperity contact with the electrodes 44 of the other layer 22.

Other techniques for providing electrical contact may be used.

FIG. 19*c* shows a perspective view and a cross section view of the two bonded layers 22 with discontinuities 34. A discontinuity 34 on the top surface of the top layer 28 and the bottom surface of the bottom layer 24 are formed as discussed above. For example, the electrodes 44 are diced or cut after or before the layers 22 are bonded. Another discontinuity 34 for each layer is formed by cutting or dicing the kerf 182 though the bottom layer 24 and into the top layer 28. Any of the cutting or dicing instruments discussed above may be used, such as a laser or wire saw. The discontinuities 34 for the top and bottom layers 24, 28 on adjacent surfaces are formed by the kerf 182. The flex circuit 64 or other electrical jumper connects the electrodes across the kerf 182. In alternative embodiments, the kerf 182 extends through the top layer 28 and into the bottom layer 24. The kerf 182 is filled with polymer or gas, such as air.

Figure 19D:
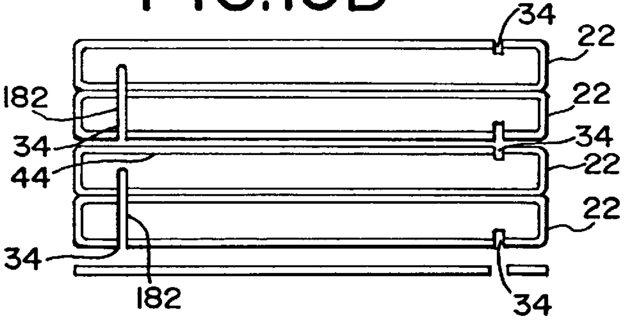
Figure 19E:
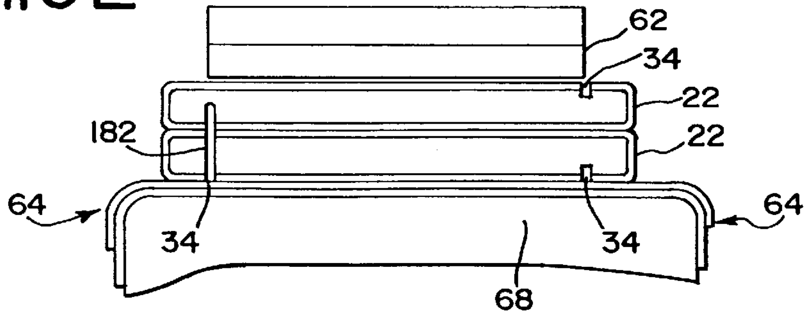

Referring to FIG. 19*e*, the bonded layers 22 with the formed discontinuities 22 are assembled with the flex circuit 64, the acoustic matching layer 62 and the backing block 68. The flex circuit 64 provides the electrical connection across the kerf 182. Where the flex circuit 64 along the bottom surface of the bottom layer 22 provides both positive and negative signal traces, a discontinuity 34 is positioned on the top surface of the top layer 22. Alternatively and as discussed above, the discontinuity 34 isolating the negative and positive electrodes is at a corner or edge surface.

Pairs of layers 22 having discontinuities formed after bonding may be stacked and bonded. FIG. 19*d* shows two pairs of layers 22 stacked. The jumper or flex circuit 64 is provided for the bottom surface of the bottom pair of layers 22. The electrode 44 of the top surface of the bottom pair of layers 22 electrically connects electrodes across the kerf 182 of the top pair of layers 22. Additional pairs or individual layers 22 may be added.

Figure 20:
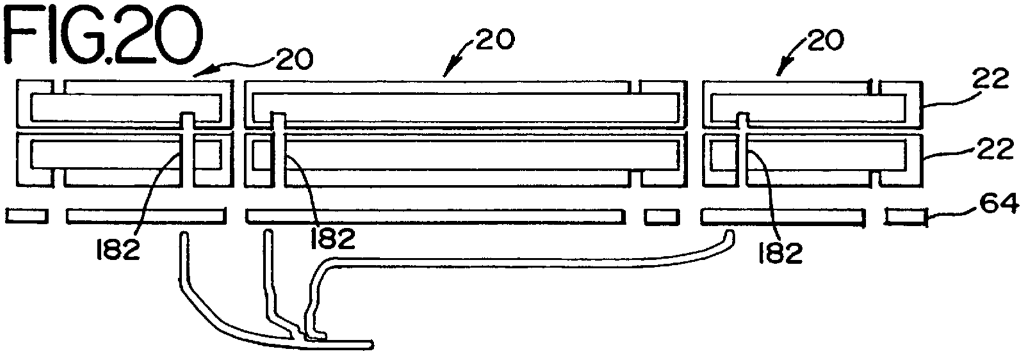
FIG. 20 is a cross section view of one embodiment of a multi-layer multi-dimensional transducer array with kerfs formed after bonding.

FIG. 20 shows a cross section of a multi-dimensional transducer array with discontinuities 34 formed after bonding. Elements 20 with two layers 22 are shown, but the elements 20 may have any even or odd number of layers 22. The kerfs 182 are cut after the layers 22 are bonded together. The flex circuit 64 jumpers the kerfs 182 on each element 20. In alternative embodiments, different jumpers are provided and/or the ground or negative signal connects to a top layer 22.

By bonding the layers 22 together before creating the discontinuities 34, the transducer material is thicker and easier to handle for dicing component. The bonded layers 22 are less fragile than each single layer 22. The individual layers 22 are handled without weakness caused by dicing the electrodes. Alignment of the layers 22 is provided by the kerf 180, 182 rather than a high tolerance alignment process after the discontinuities 34 are created. Thus, the surface area of the minority electrode may be minimized.

VI. Elevation Side Lobe Control

Multi-layer transducer elements may be formed to control generation of elevation side lobes during acoustic transmission. U.S. Pat. Nos. 5,410,208 and 5,706,820, assigned to the assignee of the present invention, the disclosures of which are incorporated herein by reference, disclose elevation side lobe control techniques. The teachings of each of these two patents may be used separately or combined.

Figure 21A:
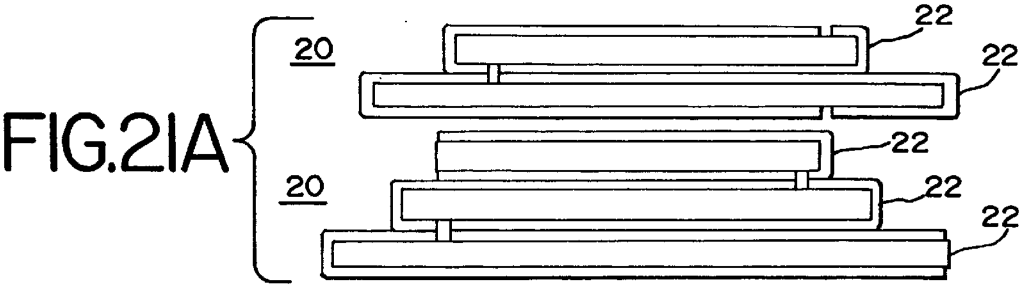
FIGS. 21*a–d* are cross section views of different embodiments of multilayer elements designed for elevation side lobe reduction.

In one embodiment, an upper surface of transducer material has less surface area than a lower surface. FIGS. 21*a* and *b* show two and three layers 22 of transducer material with different surface areas along the range dimension. For example, the elevation width of each layer 22 has a greater width for the bottom layer 22 than for the middle or top layer 22 as shown in FIG. 21*a*. The surface area of the top layer 22 is less than for the bottom or middle layer 22. Two or more of the layers 22 may have same or similar surface areas and corresponding elevational widths.

Figure 21B:
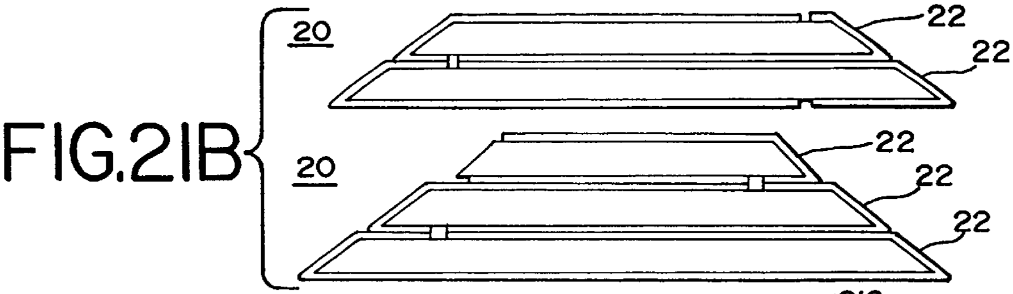

As another example, a top layer 22 or each layer 22 has sides at an angle greater than about 90 degrees and less than about 120 degrees relative to a primary acoustic propagation direction or relative to the range axis as shown in FIG. 21*b*. Each layer 22 has tapered edges along one or more sides. The surface area of each layer 22 and the element 20 in the azimuth-elevation plane is smaller as a function of range position. The upper surface areas are smaller than the bottom surface areas.

In alternative embodiments, four or more layers of transducer material are provided. In yet another alternative embodiment, one, more or all the elements 20 of a multi-dimensional transducer array include an upper surface of transducer material that has less surface area than a lower surface.

Figure 21C:
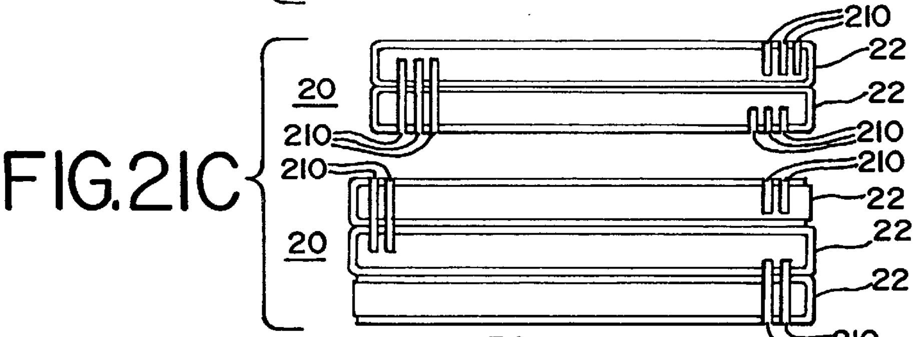

FIG. 21*c* shows kerfs 210 in one or more layers 22 of elements 20. Two or three layers 22 are shown but additional numbers of layers 22 may be used. The kerfs 210 are separated or spaced along the elevation dimension for narrowing the elevation spacing of transmitted acoustic energy. One or more kerfs 210 are diced or formed adjacent one or both elevation edges of one or more layers 22. For example, two or three kerfs 210 are formed at each elevation edge of each layer 22. The kerfs 210 extend through a substantial portion of or through the entire layer 22. The kerfs 210 are formed as discussed above to create discontinuities or are provided with jumpers to provide positive and negative electrodes for each layer 22.

Figure 21D:
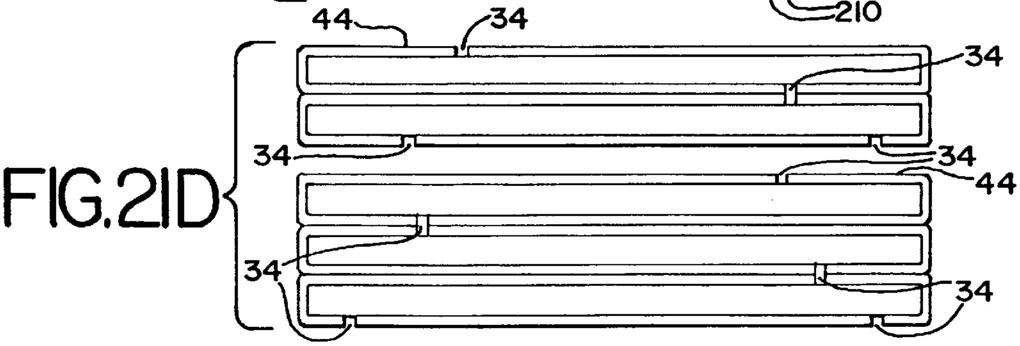

In another embodiment shown in FIG. 21*d*, the discontinuities 34 are positioned so that the active portion of the transducer material of each layer 22 provides different surface areas. The discontinuities 34 are spaced further from elevation edges of the transducer material or layers 22 as a function of the range dimension. The surface area of the minority electrode 44 is larger for upper or top layers 22 or surfaces than for lower or bottom layers 22 or surfaces.

While the invention has been described above by reference to various embodiments, it will be understood that many changes and modifications can be made without departing from the scope of the invention. For example, different manufacturing and assembly techniques may be used. Any combination of one or more of providing air between elevationally or azimuthally spaced elements, using the plunge cuts described above, elevation side lobe control, even or odd numbers of elements, opposite pole on opposite surfaces or a same surface, isolation of electrodes after bonding, using substantially similar layers and asperity contact may be used.

It is therefore intended that the foregoing detailed description be understood as an illustration of the presently preferred embodiments of the invention, and not as a definition of the invention. It is only the following claims, including all equivalents, that are intended to define the scope of the invention.

What is claimed is:

1. In a multi-layered transducer array, an improvement comprising at least one element including at least two layers of transducer material;

each of the layers comprising at least two electrodes separated by two discontinuities, a configuration of the at least two electrodes and two discontinuities being substantially the same for each layer.

2. The transducer of claim 1 wherein the transducer material comprises piezoelectric material.

3. The transducer of claim 1 wherein the at least two layers are polymericly bonded and electrical connecting asperity contact.

4. The transducer of claim 1 wherein the transducer comprises a single one-dimensional array of elements.

5. The transducer of claim 1 wherein the transducer comprises a multi-dimensional array of elements.

6. The transducer of claim 5 wherein at least two elevationally spaced elements are separated by air.

7. The transducer of claim 1 wherein the layers comprise at least two layers of equal thickness in the range dimension.

8. The transducer of claim 1 wherein a thickness along a range dimension of the element varies.

9. The transducer of claim 5 comprising a partially manufactured transducer wherein at least two elevationally spaced elements are separated by a partial through cut and held relative to each other by an uncut bridge of transducer material.

10. The transducer of claim 1 wherein a first electrical lead from an ultrasound system is adjacent to a top layer of the layers and a second electrical lead from the ultrasound system is adjacent to a bottom layer of the layers.

11. The transducer of claim 1 wherein the element comprises an even number of layers of transducer material.

12. The transducer of claim 1 wherein each of the layers comprises at least a majority and a minority electrode on both of top and bottom surfaces.

13. A method for manufacturing a multi-layered transducer array, the method comprising the acts of:

(a) stacking at least two layers of transducer material; and (b) configuring the layers with at least two electrodes and two discontinuities substantially the same for each layer.

14. The method of claim 13 further comprising:

(c) assembling the transducer array with the stacked layers, the transducer array comprising a multi-dimensional array of elements; and (d) separating first and second elevationally adjacent elements of the assembled stacked transducer with air.

15. The method of claim 13 further comprising:

(c) cutting through the first layer of transducer material along only a portion of an azimuth width of the first layer.

16. The method of claim 13 further comprising:

(c) connecting a first electrical lead from an ultrasound system adjacent to a top layer of the layers; and (d) connecting a second electrical lead from the ultrasound system adjacent to a bottom layer of the layers.

17. The method of claim 13 further comprising:

(c) stacking only an even number of layers of transducer material.

18. The method of claim 13 further comprising:

(c) providing at least a majority and a minority electrode on both of top and bottom surfaces of each of the layers.

19. The method of claim 13 further comprising:

(c) bonding the stacked layers; and (d) dicing through two layers of the stacked layers after (c);

wherein (d) electrically isolates two electrodes associated with each of the two layers.

20. The method of claim 13 further comprising:

(c) electrically connecting first and second layers with asperity contact.

21. In a multi-layered transducer array, an improvement comprising at least one element including at least two layers of transducer material;

each of the layers comprising at least a majority and a minority electrode on both of top and bottom surfaces relative to a direction of acoustic energy propagation.

22. The transducer of claim 21 wherein the transducer material comprises piezoelectric material.

23. The transducer of claim 21 wherein the at least two layers are joined by asperity contact.

24. The transducer of claim 21 wherein the transducer comprises a single one-dimensional array of elements.

25. The transducer of claim 21 wherein the transducer comprises a multi-dimensional array of elements.

26. The transducer of claim 25 wherein at least two elevationally spaced elements are separated by air.

27. The transducer of claim 21 wherein the layers comprise at least two layers of equal thickness in the range dimension.

28. The transducer of claim 21 wherein a thickness along a range dimension of the element varies.

29. The transducer of claim 25 comprising a partially manufactured transducer wherein at least two elevationally spaced elements are separated by a partial through cut and held relative to each other by an uncut bridge of transducer material.

30. The transducer of claim 21 wherein a first electrical lead from an ultrasound system is adjacent to a top layer of the layers and a second electrical lead from the ultrasound system is adjacent to a bottom layer of the layers.

31. The transducer of claim 21 wherein the element comprises an even number of layers of transducer material.

32. The transducer of claim 21 wherein each of the layers comprises at least two electrodes separated by two discontinuities, a configuration of the at least two electrodes and two discontinuities being substantially the same for each layer.

33. A method for manufacturing a multi-layered transducer array, the method comprising the acts of:

(a) stacking at least two layers of transducer material; and (b) providing at least a majority and a minority electrode on both of top and bottom surfaces of each of the layers, the top and bottom relative to the direction of propagation of acoustic energy.

34. The method of claim 33 further comprising:

(c) assembling the transducer array with the stacked layers, the transducer array comprising a multi-dimensional array of elements; and (d) separating first and second elevationally adjacent elements of the assembled stacked transducer with air.

35. The method of claim 33 further comprising:

(c) cutting through the first layer of transducer material along only a portion of an azimuth width of the first layer.

36. The method of claim 33 further comprising:

(c) connecting a first electrical lead from an ultrasound system adjacent to a top layer of the layers; and (d) connecting a second electrical lead from the ultrasound system adjacent to a bottom layer of the layers.

37. The method of claim 33 further comprising:

(c) stacking only an even number of layers of transducer material.

38. The method of claim 33 further comprising:

(c) configuring the layers with at least two electrodes and two discontinuities substantially the same for each layer.

39. The method of claim 33 further comprising:

(c) bonding the stacked layers; and (d) dicing through two layers of the stacked layers after (c);

wherein (d) electrically isolates two electrodes associated with each of the two layers.

40. The method of claim 33 further comprising:

(c) electrically connecting first and second layers with asperity contact.

* * * * *